(12) United States Patent
Cheng et al.

(10) Patent No.: US 12,099,066 B2
(45) Date of Patent: Sep. 24, 2024

(54) METHODS FOR ANALYZING BODY FLUID PROTEOME

(71) Applicants: JIANGSU QLIFE MEDICAL TECHNOLOGY GROUP CO., LTD., Jiangsu (CN); NANJING QLIFE MEDICAL TECHNOLOGY CO., LTD., Jiangsu (CN)

(72) Inventors: Xiaoliang Cheng, Nanjing (CN); Yue Zhou, Nanjing (CN); Wei Zhang, Nanjing (CN); Kejia Zheng, Nanjing (CN)

(73) Assignees: JIANGSU QLIFE MEDICAL TECHNOLOGY GROUP CO., LTD., Nanjing (CN); NANJING QLIFE MEDICAL TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 18/301,279

(22) Filed: Apr. 17, 2023

(65) Prior Publication Data
US 2023/0258654 A1    Aug. 17, 2023

Related U.S. Application Data

(63) Continuation of application No. PCT/CN2021/129619, filed on Nov. 9, 2021.

(51) Int. Cl.
*G01N 33/68* (2006.01)

(52) U.S. Cl.
CPC ..... *G01N 33/6848* (2013.01); *G01N 2570/00* (2013.01)

(58) Field of Classification Search
None
See application file for complete search history.

(56) References Cited

U.S. PATENT DOCUMENTS

| | | |
|---|---|---|
| 2003/0211483 A1 | 11/2003 | Schroeder et al. |
| 2004/0209380 A1 | 10/2004 | Bente |

(Continued)

FOREIGN PATENT DOCUMENTS

| | | |
|---|---|---|
| CN | 101694485 A | 4/2010 |
| CN | 104880546 A | 9/2015 |

(Continued)

OTHER PUBLICATIONS

Cai, T. et al. Strategies for Characterization of Low-Abundant Intact or Truncated Low-Molecular-Weight Proteins From Human Plasma, The Enzymes, vol. 42, Chapter Five, 105-123 (Year: 2017).*

(Continued)

*Primary Examiner* — Xiaoyun R Xu
(74) *Attorney, Agent, or Firm* — METIS IP LLC

(57) ABSTRACT

The embodiments of the present disclosure provide a method for analyzing a body fluid proteome. The method comprises: obtaining a sample to be tested I enriched with low-abundance proteins by removing high-abundance proteins in an initial sample A using an affinity technique; obtaining a sample to be tested II enriched with low-abundance proteins by removing high-abundance proteins in an initial sample B using chemical precipitation, wherein the initial sample A and the initial sample B are obtained from a same body fluid sample of a same subject; obtaining a proteome data set I by performing proteomic analysis on the sample to be tested I; obtaining a proteome data set II by performing proteomic analysis on the sample to be tested II; and determining a final quantified proteome data set of the body fluid sample based on the proteome data set I and the proteome data set II.

19 Claims, 12 Drawing Sheets

(56) References Cited

U.S. PATENT DOCUMENTS

| | | | |
|---|---|---|---|
| 2011/0237459 A1* | 9/2011 | Nova | C40B 30/04 506/7 |
| 2019/0317059 A1 | 10/2019 | Zhang et al. | |

FOREIGN PATENT DOCUMENTS

| | | |
|---|---|---|
| CN | 104974218 A | 10/2015 |
| CN | 111537658 A | 8/2020 |
| CN | 111896646 A | 11/2020 |
| CN | 111902720 A | 11/2020 |
| CN | 112014198 A | 12/2020 |
| CN | 112710755 A | 4/2021 |

OTHER PUBLICATIONS

Searle, B.C. et al. Chromatogram libraries improve peptide detection and quantification by data independent acquisition mass spectrometry, Nature Communications, 9, 5128 (Year: 2018).*

Patra, M. et al. Probing Conformational Stability and Dynamics of Erythroid and Nonerythroid Spectrin: Effects of Urea and Guanidine Hydrochloride, PLOS one, journal.pone.0116991, Jan. 24, 2015 (Year: 2015).*

Hu, Diefei et al., Optimization of the Method of Removing High and Medium Abundance Proteins from Serum, Journal of Guangxi Medical University, 2011, 6 pages.

Ma, Meilan et al., Research on Using Two Methods to Remove the High-abundant Proteins in Serum of Lung Cancer, Gansu Medical Journal, (35) 1: 4-6, 2016.

Rpingels, Lentel et al., Abundant plasma protein depletion using ammonium sulfate precipitation and Protein A affinity chromatography, Journal of Chromatography B, 1089: 43-59, 2018.

Fu, Qin et al., A Rapid, Economical, and Reproducible Method for Human Serum Delipidation and Albumin and IgG Removal for Proteomic Analysis, Methods in Molecular Biology, 357: 365-371, 2007.

International Search Report in PCT/CN2021/129619 mailed on Apr. 24, 2022, 10 pages.

Written Opinion in PCT/CN2021/129619 mailed on May 19, 2022, 8 pages.

Zhang, Bin et al., Comparative Study of Four Sample Preparation Methods for Separating Rat Serum Protein by 2-DE, Chinese Journal of Laboratory Diagnostics, 16(9): 1544-1547, 2012.

Yue Zhou et al., High-Throughput, In-Depth and Estimated Absolute Quantification of Plasma Proteome Using Data-Independent Acquisition/Mass Spectrometry ("HIAP-DIA"), Proteomics, pp. 1-12, 2021.

Wang Jun et al., Removal of High-Abundance Proteins in Plasma of the Obese by Improved TCA/Acetone Precipitation Method, Journal of Hygiene Research, 42(5): 741-747, 2013.

* cited by examiner

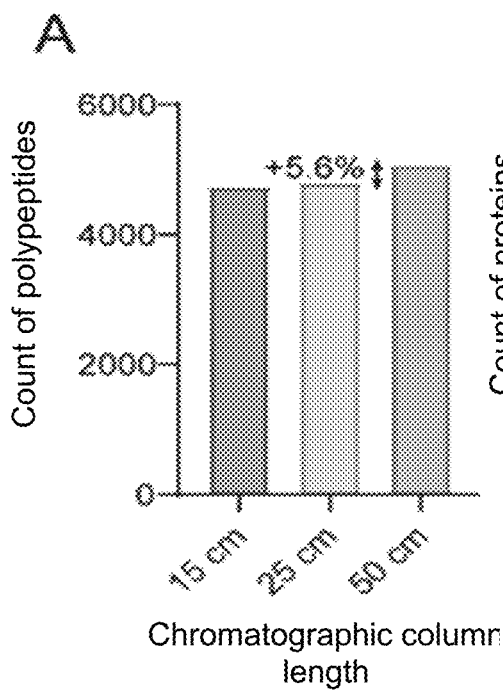
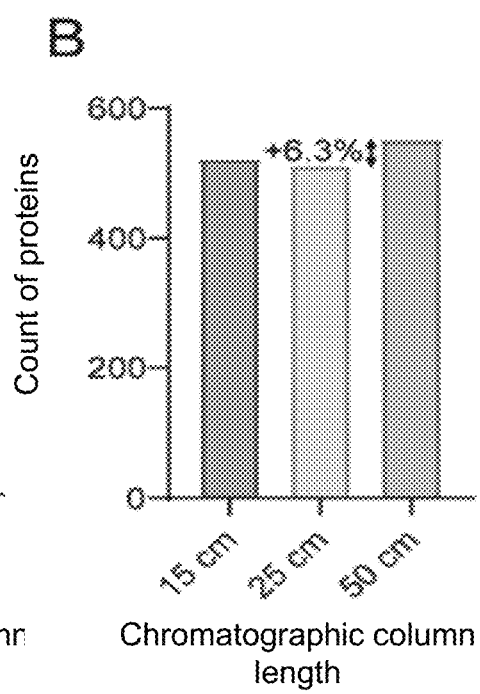
FIG. 2A FIG. 2B
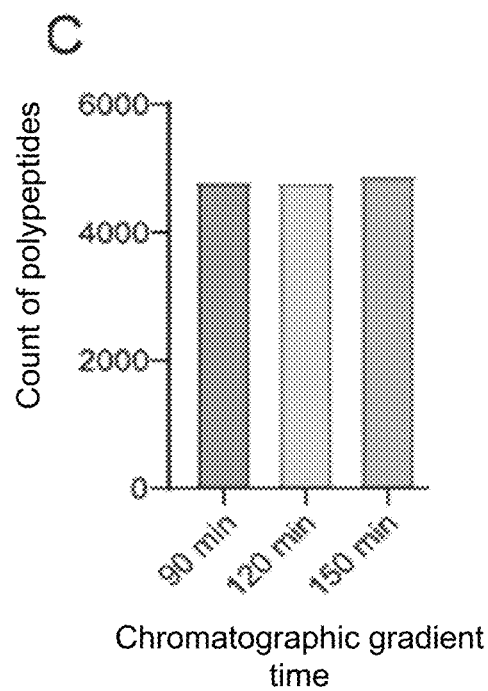
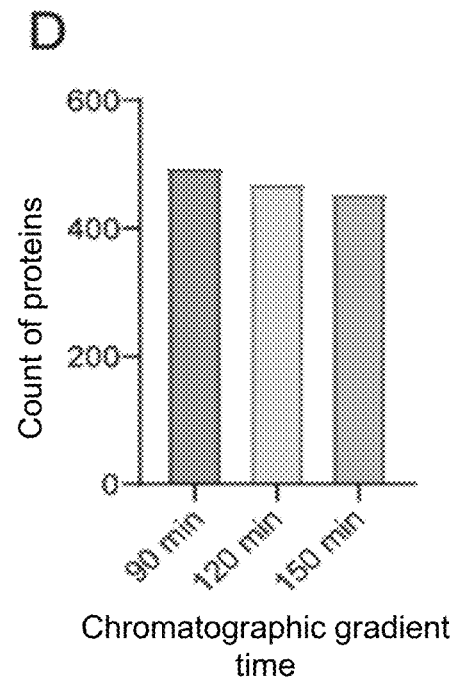
FIG. 2C FIG. 2D

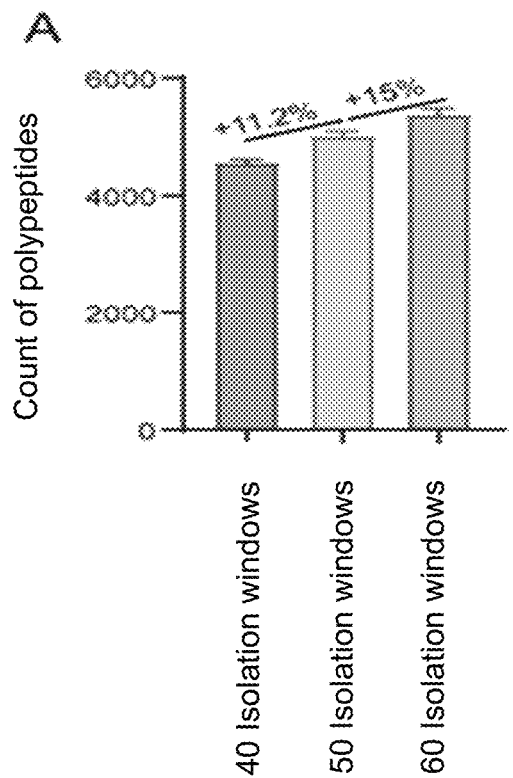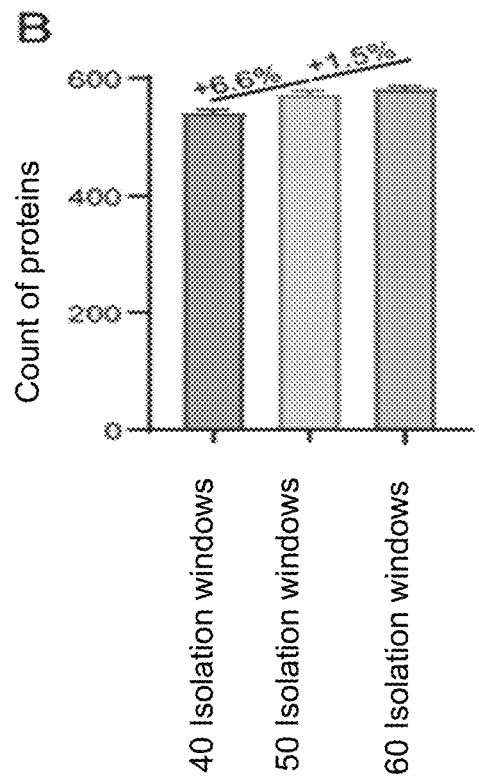
FIG. 3A
FIG. 3B
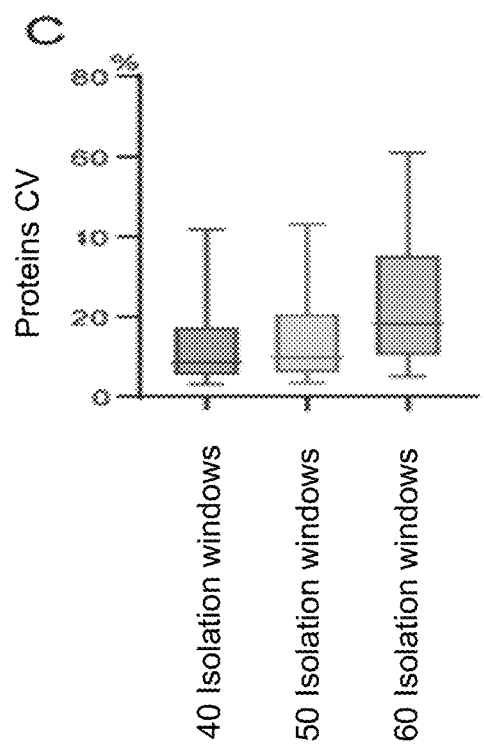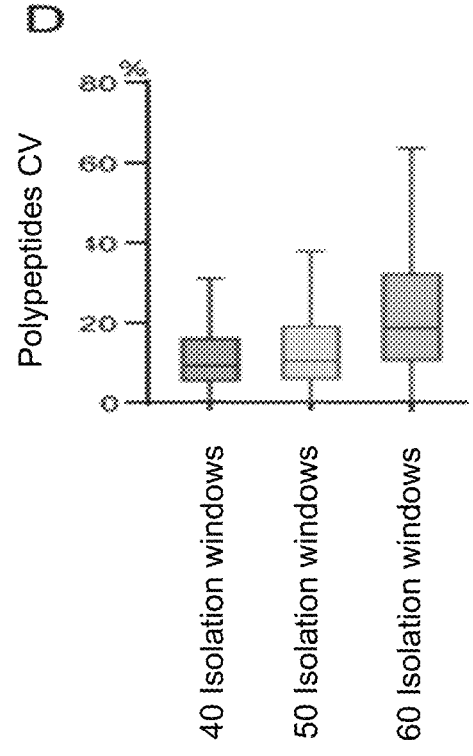
FIG. 3C
FIG. 3D

METHODS FOR ANALYZING BODY FLUID PROTEOME

CROSS REFERENCE TO RELATED APPLICATION

This application is a Continuation of International Patent Application No. PCT/CN2021/129619, filed on Nov. 9, 2021, the entire contents of which are hereby incorporated by reference.

TECHNICAL FIELD

The present disclosure belongs to the field of biochemical detection, and in particular to methods for analyzing a body fluid proteome.

BACKGROUND

Plasma and serum in body fluids are usually used for clinical diagnosis and prognostic analysis. Plasma proteins can be used as indicators of individual health status and as biomarkers for clinical detection. More and more studies have focused on plasma proteins. Plasma proteomics is a powerful tool for the study of plasma proteins, which can be used for the identification and quantitative analysis of a plurality of proteins in clinical samples with high flux.

Clinical studies often require quantitative proteomic analysis of hundreds or thousands of samples and increased coverage of proteomes, to develop more plasma biomarkers. However, various technical difficulties in the existing techniques (e.g., the inability to efficiently remove high-abundant proteins (HAPs) that cause interference) often restrict the sample analysis fluxes. Currently, the coverage of plasma proteome reported is 500-1000 proteins, which limits the development of plasma protein markers. Therefore, it is desirable to develop new methods and systems to improve the flux and efficiency of proteome analysis.

SUMMARY

In some embodiments, a method for analyzing a body fluid proteome may include:

obtaining a sample to be tested I enriched with low-abundant proteins (LAPs) by removing HAPs in an initial sample A using an affinity technique;

obtaining a sample to be tested II enriched with LAPs by removing HAPs in an initial sample B using chemical precipitation, wherein the initial sample A and the initial sample B are obtained from a same body fluid sample of a same subject;

obtaining a proteome data set I by performing proteomic analysis on the sample to be tested I using an optimized data independent acquisition (DIA) technique;

obtaining a proteome data set II by performing proteomic analysis on the sample to be tested II using an optimized DIA technique; and determining a final quantified proteome data set of the body fluid sample based on the proteome data set I and the proteome data set II.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, wherein:

FIGS. 2A-2F illustrates results of plasma proteome analysis using a DIA technique according to some embodiments of the present disclosure, wherein FIG. 2A and FIG. 2B illustrate a count of polypeptides and proteins identified by DIA under the conditions of chromatographic columns of 15 cm, 25 cm, and 50 cm, and a gradient of 90 min; FIG. 2C and FIG. 2D illustrate a count of polypeptides and proteins identified under the conditions of a chromatographic column of 25 cm, and gradients of 90 min, 120 min, and 150 min; FIG. 2E and FIG. 2F illustrate a count of polypeptides and proteins identified under the conditions of a chromatographic column of 50 cm and gradients of 90 min, 120 min, and 150 min;

FIGS. 3A-3D illustrate results of plasma proteome analysis using a DIA technique according to some embodiments of the present disclosure, wherein FIG. 3A and FIG. 3B illustrate a count of polypeptides and proteins identified under the conditions of 40, 50 and 60 isolation windows, respectively; FIG. 3C and FIG. 3D illustrate a coefficient of variation (CV) distribution of protein intensity and a CV distribution of polypeptide intensity identified under the conditions of 40, 50, and 60 isolation windows, respectively;

FIGS. 7A-7C illustrate a coverage of a final quantified proteome data set by a method for analyzing a body fluid proteome according to some embodiments of the present disclosure; wherein FIG. 7A illustrates an FDA-approved biomarker covered by a final quantified proteome data set; FIG. 7B illustrates a brain tissue specific protein covered by a final quantified proteome data set; and FIG. 7C illustrate a liver specific protein covered by a final quantified proteome data set.

DETAILED DESCRIPTION

Body fluids such as serum, plasma, and cerebrospinal fluid are commonly used samples in the field of proteomics research based on mass spectrometry. Such samples contain a rich variety of proteins, among which HAPs account for 97%-99%, including albumin, IgG, IgA, fibrinogen, transferrin, haptoglobin, anti-trypsin, etc. However, LAPs are often disease specific biomarkers or target protein molecules. Therefore, removing the HAPs that interfere with detection and enriching as many the LAPs as possible have become one of the key factors for the quantity identified by mass spectrometry.

To solve this problem, the commonly used techniques for removing the HAPs include affinity technique, chemical precipitation, ultrafiltration centrifugation, goldmag particles, isoelectric capture, liquid chromatography, etc. The affinity technique achieves the purpose of separating or removing target proteins from samples through the specific affinity between the immobilized ligands and the target proteins. The chemical precipitation achieves the purpose of removing the HAPs in the samples by adding a precipitant to precipitate the proteins. The precipitant can be an organic solvent or an ammonium salt. The liquid chromatography is mostly used for protein separation. The commonly used ion exchange chromatography and size exclusion chromatography remove proteins by using different sizes and charges of protein molecules.

The DIA technique is a new mass spectrometry technique developed in recent years, which belongs to the label-free proteomics method. The DIA technique adopts the data independent scanning mode: the entire full scanning range of the mass spectrum is divided into several windows, and then all ions in each window are detected and fragmented, so as to obtain the information of all ions in the samples without omission or difference. The DIA technique can reduce the missing value during sample detection, and improve quantitative accuracy and repeatability, thereby achieving high-stability and high-precision quantitative analysis of proteomes in large sample cohorts. The DIA technique has been used more frequently in plasma proteomics due to the above advantages.

One of the objectives of the present disclosure is to provide a method for analyzing a body fluid proteome.

Figure 1:
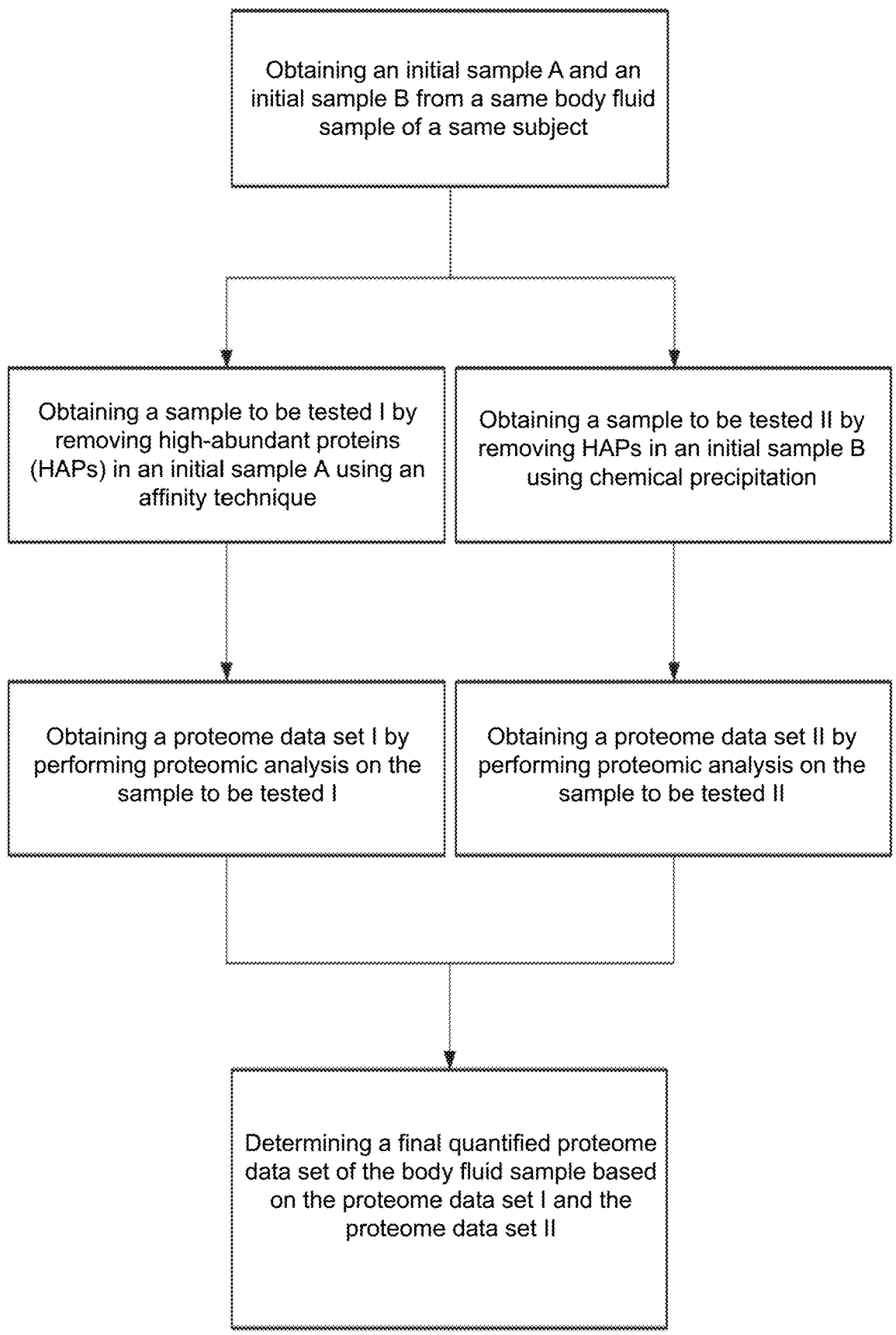
FIG. 1 is a flowchart illustrating a method for analyzing a body fluid proteome according to some embodiments of the present disclosure.

In some embodiments, as shown in FIG. 1, the method for analyzing the body fluid proteome may include:

obtaining a sample to be tested I enriched with LAPs by removing HAPs in an initial sample A using an affinity technique;

obtaining a sample to be tested II enriched with LAPs by removing the HAPs in an initial sample B using chemical precipitation, wherein the initial sample A and the initial sample B are obtained from a same body fluid sample of a same subject;

obtaining a proteome data set I by performing proteomic analysis on the sample to be tested I; obtaining a proteome data set II by performing proteomic analysis on the sample to be tested II; and determining a final quantified proteome data set of the body fluid sample based on the proteome data set I and the proteome data set II.

In some embodiments, the performing the proteomic analysis on the sample to be tested I may include: performing quantitative proteomic analysis on the sample to be tested I using a DIA technique. In some embodiments, the performing the proteomic analysis on the sample to be tested II may include: performing quantitative proteomic analysis on the sample to be tested II using the DIA technique.

In some embodiments, a peptide set I for proteomic analysis using the DIA technique may be obtained after the sample to be tested I is reduced, alkylated, digested, and desalted. In some embodiments, a peptide set II for proteomic analysis using the DIA technique may be obtained after the sample to be tested II is desalted, reduced, alkylated, and digested.

In some embodiments, the DIA technique may be an optimized DIA technique; and the optimized DIA technique may use a chromatographic column length of 50 cm and a chromatographic column gradient of 90 min. In some embodiments, the optimized DIA technique may use a chromatographic column length of 50 cm and a chromatographic column gradient of 150 min. In some embodiments, the optimized DIA technique may use a chromatographic column length of 50 cm and a chromatographic column gradient of 120 min. In some embodiments, in the optimized DIA technique, an MS1 resolution may be set to 60 K, an MS2 resolution may be set to 30 K, and a precursor ion scanning range may be set to m/z 350-1200 and divided into 50 windows.

In some embodiments, the removing HAPs in an initial sample A using an affinity technique may include: removing the HAPs by using antibodies to the HAPs as affinity ligands. In some embodiments, the HAPs may include one or more of albumin, IgA, IgD, IgE, IgG, IgM, α1-acid glycoprotein, α1-antitrypsin, α2-macroglobulin, apolipoprotein A1, fibrinogen, haptoglobin, transferrin, complement C3, apolipoprotein A-II, α-2-HS-glycoprotein, apolipoprotein C-III, α-1-antichymotrypsin, a vitamin D-binding protein, ceruloplasmin, complement C4-A, complement C1q, hemagglutinin, kininogen-1, synaptotagmin 5, histidine-rich glycoprotein, vitronectin, a complement factor H, a plasma protease C1 inhibitor, C4b binding protein, and fibronectin.

In some embodiments, the antibodies to the HAPs may be immobilized on solid phase carriers. In some embodiments, the solid phase carriers may include one or more of cellulose, polyacrylamide, polystyrene, polyethylene, polypropylene, cross-linked dextran, glass, silicone rubber, agarose gel, and a gel resin. In some embodiments, the solid phase carriers may be gel resins. In some embodiments, a plurality of HAPs may be removed at one time by immobilizing the antibodies to the plurality of HAPs on the solid phase carriers. In some embodiments, 31 types of HAPs may be removed at one time by immobilizing the antibodies to the 31 types of HAPs on the solid phase carriers, thereby improving the efficiency, and reducing the cost.

In some embodiments, the removing the HAPs in the initial sample A using the affinity technique may be carried out in a multi-cavity vessel. In some embodiments, the removing the HAPs in the initial sample B using the chemical precipitation may be carried out in a multi-cavity vessel. In some embodiments, the multi-cavity vessel may be a multiwell plate, such as a 96-well plate, 48-well plate, or a 24-well plate. By using a method for removing the HAPs based on the multiwell plate, a plurality of samples can be processed at a time, such as 2×96 samples, thereby improving the flux of proteome analysis.

In some embodiments, the body fluid sample may include a plasma sample, a serum sample, a urine sample, an interstitial fluid sample, an intrapleural fluid sample, an intraperitoneal fluid sample, a cerebrospinal fluid sample, a semen sample, a vaginal fluid sample, or the like, or any combination thereof.

In some embodiments, the removing the HAPs in the initial sample B using the chemical precipitation may include: precipitating the HAPs by using an organic solvent as a precipitating agent. In some embodiments, the organic solvent may include methanol, ethanol, isopropanol, acetonitrile, chloroform, trichloroacetic acid, and trifluoroacetic acid, or the like, or any combination thereof.

In some embodiments, the removing the HAPs in the initial sample B using the chemical precipitation may further include: denaturing the HAPs using a denaturant before precipitating the HAPs by using the precipitating agent. In some embodiments, the denaturant may include at least one of guanidine hydrochloride and urea.

In some embodiments, the determining a final quantified proteome data set of the body fluid sample based on the proteome data set I and the proteome data set II may include obtaining a proteome data set III by removing overlapping data of the proteome data set II with the proteome data set I from the proteome data set II; and using the proteome data set I and the proteome data set III as the final quantified proteome data set of the body fluid sample. In some embodiments, the removing overlapping data of the proteome data set II with the proteome data set I from the proteome data set II may include: obtaining the proteome data set III by comparing the proteome data set I with the proteome data set II through a Venn diagram, and removing the overlapping data of the proteome data set II with the proteome data set I from the proteome data set II. In some embodiments, the overlapping data of the proteome data set II with the proteome data set I may be overlapping protein data of the proteome data set II and the proteome data set I.

In some embodiments, the methods of the present disclosure may be used for non-diagnostic applications.

In some embodiments, the subject may include at least one of a human being and a non-human mammal.

The method for analyzing the body fluid proteome provided in some embodiments has good reproducibility and high coverage of plasma proteome, quantifying more than 1,700 types of proteins.

EXAMPLE

Plasma Collection

Blood samples were collected from healthy subjects, a citrate/blood mixture (1:9, v/v) was centrifuged (3000 rpm) at 10° ° C. for 10 min, and stored at −80° C. for later use.

Removal of HAPs Based on Antibody Affinity (1) Preparation of Gel Resins 150 mg of dry Pierce™ NHS-Activated gel resins (purchased from Thermo Fisher, USA) were put into an empty spin column, and 2 mL of each solution containing 1 mg/mL antibodies to the following proteins was added into the spin column. The proteins includes albumin, IgA, IgD, IgE, IgG, IgM, α1-acid glycoprotein, α1-antitrypsin, α2-macroglobulin, apolipoprotein A1, fibrinogen, haptoglobin, transferrin, complement C3, apolipoprotein A-II, α-2-HS-glycoprotein, apolipoprotein C-III, α-1-antichymotrypsin, a vitamin D-binding protein, ceruloplasmin, complement C4-A, complement C1q, hemagglutinin, kininogen-1, synaptotagmin 5, histidine-rich glycoprotein, vitronectin, a complement factor H, a plasma protease C1 inhibitor, C4b binding protein, and fibronectin. The solutions were mixed upside down and reacted for 2 hours. Each spin column was put into a collection tube and centrifuged at 1000 g for 1 min. 2 mL of a mixture of 0.1M sodium phosphate and 0.15M NaCl with pH 7.2 was added to each spin column, and centrifuged with 1000 g for 1 min, and repeated once. 1 mL of 1M Tris buffer solution with pH 7.4 was added to each spin column, mixed by inverting at room temperature for 15-20 min, and centrifuged with 1000 g for 1 min. 2 mL of a mixture of 0.1M sodium phosphate and 0.15M NaCl with pH 7.2 was added to each spin column and centrifuged with 1000 g for 1 min. 500 μL of a mixture of 0.1M sodium phosphate, 0.15M NaCl, and 0.05 wt % sodium azide with pH 7.2 was added to preserve the gel resins.

(2) Removal of HAPs in Plasma

The prepared gel resins were mixed, and 40 μL was taken to add to each well of a 0.45 μm 96-well plate. a 6 μL of 6-fold diluted plasma sample was added to each well, shook and incubated for 30 minutes, and centrifuged with 4000 g for 2 min. An eluate from each well was collected.

(3) Preparation of a Peptide Set I for DIA

A 70 μl protein lysate containing 1 wt % SDC and 100 mM Tris-HCl with pH 8.5 was added to the eluate of each well; 2 μl of 0.5 M tris(2-carboxyethyl)phosphine (TCEP) and 8 μl of 0.5 M trichloroacetic acid (TCA) solution was added to each well, reacted at 70° C. for 10 min, and then cooled to room temperature; and then a 1 μg of a Lys C/Trypsin mixed enzyme reagent was added to each well and reacted at 37° C. for 2 hours to obtain a digestion solution. A 100 μL 1% trifluoroacetic acid (TFA) solution of isopropanol (IPA) was added to the digestion solution of each well for SCX desalting. A 200 μl digestion solution was added to each well of a 96-well SCX solid phase extraction plate, and centrifuged with 1000 g for 2 min; a 400 μL 1% TFA solution of IPA in was added for eluting, centrifuged at 1000 g for 2 min, and discarded the eluent; 400 μL of 0.2% TFA was added, centrifuged with 1000 g for 2 min to rinse, and discarded the eluent; and 200 μL of a mixture of 1% ammonia and 80% acetonitrile (ACN) was added, centrifuged with 1000 g for 2 min, and collected the eluate from each well. The eluate was concentrated and dried in a freeze concentrator, and redissolved by adding 20 μL of 0.1% formic acid (FA) solution to obtain the peptide set I for DIA.

Removal of HAPs by chemical precipitation (1) Removal of HAPs in Plasma

50 μL plasma and 50 μL lysate (8 M urea, 100 mM Tris, pH8.0) were added to each well of a 96-well plate, and incubated at room temperature for 5 min; 100 μl of 20% TCA solution was added, shaken at 1500 RPM at 4°C for 60 min to precipitate proteins; and centrifuged with 4000 g, and 150 μl of supernatant from each well was taken.

(2) Preparation of Peptide Set II for DIA

The supernatant was added to each well of a 96-well HLB solid phase extraction plate, and centrifuged with 1000 g for 2 min. The supernatant was discarded. 400 μl of the 0.2% TFA solution was added to each well, and centrifuged with 1000 g for 2 min; the supernatant was discarded; and 400 μL of a mixture of 0.2% TFA and 80% ACN solution was added to each well, and centrifuged with 1000 g for 2 min to collect the eluate. The eluate was concentrated and dried in a freeze concentrator, and redissolved by adding 100 μL of 50 mM $NH_4CO_3$; 2 μl of 0.5 M TCEP and 8 μl of 0.5 M TCA were added, and reacted at 70° C. for 10 min; and 1 μg of the Lys C/Trypsin mixed enzyme reagent was added, and reacted at 37° C. for 2 h. The digestion solution was concentrated and drained in the freeze concentrator, and redissolved in 20 μL of 0.1% formic acid (FA) solution to obtain the peptide set II for DIA.

DIA Technique

DIA is to perform MS/MS fragmentation indiscriminately on all polypeptide precursor ions within a specific mass-to-charge ratio (m/z) range after a high-resolution full scan of the primary mass spectrometer. In DIA, a high-resolution MS2 spectrum is used for peptide identification. High-resolution MS1 and MS2 can be used for peptide/protein quantification. The following instrumental parameters generally need to be considered: (i) a number of isolation windows and a size of each isolation window. DIA co-isolates and co-fragments all precursor ions within a given precursor ion isolation window. Therefore, the size of the isolation window directly affects the selectivity, dynamic range and sensitivity of DIA analysis. The use of a wide isolation window can increase the accumulation time of a secondary spectrum and improve the sensitivity of analysis, which is used for the analysis of very low-abundant samples; and the use of a narrow isolation window can reduce the count of co-fragmented precursor ions and reduce interference, which is used for relatively complex samples. (ii) DIA cycle time and chromatographic peak width The cycle time in DIA may correspond to a sum of MS1 scanning time and MS2 scanning time. Accurate quantitative analysis by averaging the sum of chromatographic peak widths may require averaging 7-10 acquired data points to fit the extracted ion chromatogram to calculate an optimal DIA cycle time. For example, when an average peak width is 30 s, the cycle time may be set to 3-4 s. In DIA data analysis, a DIA quantitative spectrum library may be established. The spectrum library may include information about proteins and peptides thereof, such as retention time, precursor ions m/z, fragment ions m/z, relative abundance of fragment ions, etc. Peak extraction may be performed on the DIA data according to the information of peptides in the spectrum I library, and intensity of the peptides may be represented by a sum of peak areas of the fragment ions.

The parameters of the DIA technique may be optimized to obtain a good balance between proteome depth and flux and a balance between protein qualitation and quantification. Digested peptides from original plasma samples whose HAPs are not removed (undepleted peptides) may be used as samples for the optimization of the DIA technique.

Figure 2E:
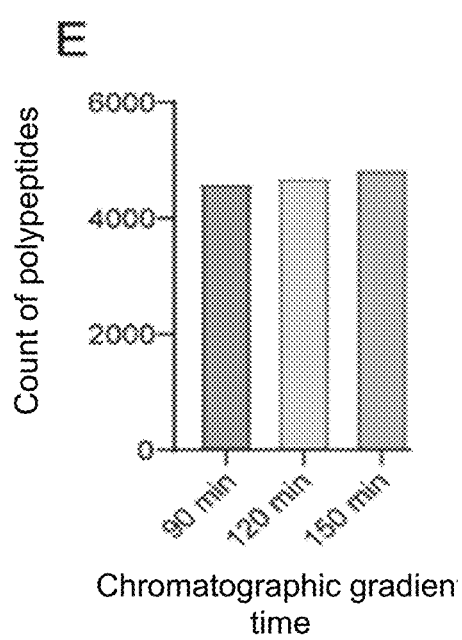
Figure 2F:
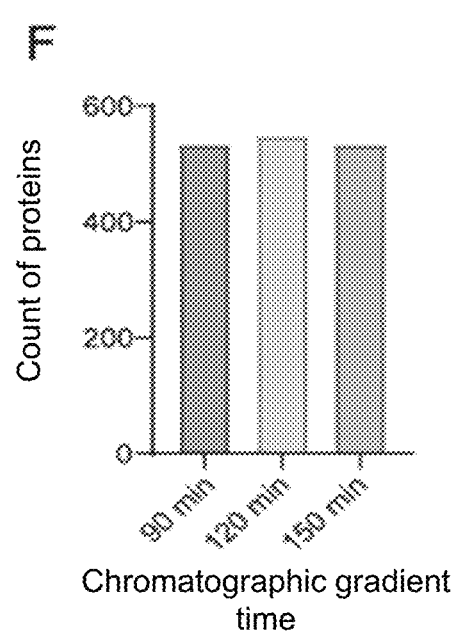

In nanochromatography with the DIA technique, a chromatographic column length and a chromatographic gradient may affect peak capacity and thus proteome depth in single-run DIA. As shown in FIG. 2A and FIG. 2B, FIG. 2A and FIG. 2B illustrate a count of polypeptides and proteins identified by DIA under the conditions of a chromatographic column of 15 cm, 25 cm and 50 cm, respectively, and a chromatographic gradient of 90 min. The highest count of peptides and proteins identified occurred when the chromatographic column length was 50 cm, which had the smallest peak width and the largest peak capacity. As shown in FIG. 2C and FIG. 2D, FIG. 2C and FIG. 2D illustrate a count of peptides and proteins identified under the condition of a chromatographic column of 25 cm and a chromatographic gradient of 90 min, 120 min, and 150 min, respectively. The count of peptides and proteins identified by using the chromatographic gradient of 150 min was equivalent to the count of peptides and proteins identified by using the chromatographic gradient of 120 min or 90 min. In order to increase the detection flux, the chromatographic gradient of 90 min was selected for plasma proteome analysis. As shown in FIG. 2E and FIG. 2F, FIG. 2E and FIG. 2F illustrate a count of peptides and proteins identified under the condition of a chromatographic column of 50 cm and a chromatographic gradient of 90 min, 120 min, and 150 min, respectively. Accordingly, the chromatographic column of 50 cm and the chromatographic gradient of 90 min were the optimal combination for plasma proteomics, presenting a good balance between the proteome depth and flux.

In the mass spectrometry of the DIA technique, a narrow DIA isolation window can improve sensitivity, but prolong the cycle time, leading to fewer peaks and poor quantitative reproducibility; on the contrary, a wide isolation window may shorten the cycle time and lead to more peaks, leading to better reproducibility, but reducing sensitivity, and thus an appropriate count of DIA isolation windows may balance qualitative and quantitative performance. The MS1 resolution was fixed at 60 K, the MS2 resolution was set to 30 K, and the precursor ion scanning range was set at m/z 350-1200. The count of DIA windows for one DIA cycle time was set to 40, 50, or 60, given that the average peak width of the optimized nanochromatogram was 0.21 min (combination of the chromatographic column of 50 cm and the chromatographic gradient of 90 min). As shown in FIG. 3A-3D, the DIA technique using 40 DIA isolation windows with the shortest cycle time gave the lowest count of identified peptides and proteins but the optimal quantitative reproducibility; the DIA technique using 60 DIA isolation windows with the longest cycle time gave the highest count of identified peptides and proteins but the worst quantitative reproducibility. Therefore, the DIA technique using 50 DIA isolation windows achieved a balance between the count of identified proteins and the quantitative reproducibility.

The peptide set I and the peptide set II were analyzed by mass spectrometry using an optimized DIA technique, to obtain a proteome data set I and a proteome data set II, respectively.

DIA chromatography: 4 μL of the redissolved peptides was loaded onto a nanoliter chromatographic column with an inner diameter of 75 μm, a length of 50 cm, and a filler of 1.9 μm Reprosil-Pur C18. A mobile phase A of Ultimate 3000 RSLC nano was 0.1% formic acid/$H_2O$, and a mobile phase B was 80% ACN/0.1% formic acid. The gradient was 0-4 min, 3-6% of the mobile phase B; 4-83 min, 6-30% of the mobile phase B; 83-87 min, 30%-90% of the mobile phase; 87-90 min, 90%-90% of the mobile phase. The total gradient was 90 min. The total gradient was set to 120 min or 150 min by adjusting the time corresponding to the 6-30% of the mobile phase B.

DIA Mass spectrometry (MS) was completed by Orbitrap mass spectrometry. Each MS cycle time consists of a complete full-scan MS (R 60,000 @ m/z 200, AGC of 2e5, maximum ion inject time of 20 ms, and mass range of 350-1,200) and 50 DIA scans (R 30,000 @ m/z 200, AGC of 5E5, maximum ion inject time of 55 ms, normalized collision energy (NCE) of 32, and mass range of 200-2,000), with the cycle time of 3.4 s.

Establishment of plasma spectrum library with deep coverage: 200 μg of the peptide set I and the peptide set II were dissolved in 50 μL 10 mM $NH_3 \cdot H_2O$, respectively, and then loaded onto an Xbridge BEH300 C18 column at a flow rate of 100 μL/min using ultimate 3000 HPLC, and chromatographically separated. A buffer solution A was 10 mM $NH_3 \cdot H_2O$; a buffer solution B was 10 mM $NH_3 \cdot H_2O$ in 90% ACN. The gradient was 0-4 min, 2-2% of B; 4-50 min, 2-30% of B; 50-58 min, 30%-90% of B; 58-60 min, 90%-

90% of B; 60-65 min, 2%-2% of B. Fractions from 4-58 min were collected manually at 1 min intervals. The solution to be analyzed was lyophilized in a vacuum freeze concentrator and dissolved in 10 μL of 0.1% FA for LC-MS/MS analysis. 5 μL of polypeptides was loaded onto a laboratory-made chromatographic column with an inner diameter of 75 μm, a length of 30 cm, and a filler of 3 μm Reprosil-Pur C18. The mobile phase A was 0.1% formic acid/$H_2O$ and the mobile phase B was 80% ACN/0.1% formic acid. The gradient was 0-4 min, 3-6% of B; 4-83 min, 6-30% of B; 83-87 min, 30%-90% of B; 87-90 min, 90%-90% of B. The total gradient was 90 min. The mass spectrometry data was collected using data dependent acquisition (DDA) mode of Orbitrap Fusion Lumos Tribrid MS with the following parameters: spray voltage was 2 kV; S-lens RF was 30; capillary temperature was 300° C.; the full-scan resolution was 60 000 @ m/z 200 and automatic gain control (AGC) was 4e5, and the maximum ion inject time was 30 ms; the mass range was 350-1500; the scanning resolution was 15000 @ m/z 200; the longest ion inject time of a secondary scan was 30 ms and the AGC was 5e4; the starting m/z of the secondary scan was 110; HCD fragmentation NCE was 30; MIPS was "peptide"; the parent ions with a charge number of 2-7 were selected for secondary mass spectrometry acquisition; dynamic exclusion time was 40 s; and DDA cycle time was 3 s. DDA database retrieval was performed using a MaxQuant software package (V. 1.5.6.0), with FDR set to 1% for proteins and peptides. For peptide identification, a minimum length of 6 amino acids and a maximum mass of 10 000 Da were required; retrieval was performed using the Andromeda search engine; the database was a Swiss-Prot human database (V. 201502; 20,534 protein sequences) and 262 common contaminating protein sequences; enzyme specificity was set to the C-terminal digestion of arginine and lysine, with a maximum of 2 missed digestion sites; Carbamidomethylation (C) was set as a fixed modification, and oxidation (M) was set as a variable modification; and the "match between run (MBR)" and "second peptide" functions were enabled. the DDA results of MaxQuant were imported into Spectronaut V13 of the Biognosys Company, and a minimum of 3 and a maximum of 6 fragment ions were selected for each parent ion; and m/z was set to 350-1800.

Deep coverage plasma spectrums constructed by the peptide set I and the peptide set II were separately analyzed, which contained information about proteins and peptides thereof, such as retention time, a precursor ion mass-to-charge ratio, a fragment ion mass-to-charge ratio, and relative abundance of fragment ions, etc.

TABLE 1

Plasma proteome spectrum library of peptide set I and peptide set II

| Sample | Count of precursor ions | Polypeptide | Protein |
|---|---|---|---|
| Peptide set I | 77,840 | 52,986 | 5,106 |
| Peptide set II | 19,436 | 15,708 | 1,325 |

Target peak extraction of the DIA data of the peptide set I and the peptide set II were extracted with Spectronaut V13 from the Biognosys Company, and the deep coverage plasma proteome spectrum libraries constructed from the peptide set I and the peptide set II were used respectively. Carbamidomethylation was set as fixed modification, and methionine Oxidation was set as variable modification. Enzyme digestion was performed using Trypsin, with a maximum of 2 missed digestion sites. The FDR for controlling the polypeptide and protein levels was 1%. An average of 3 peptides with the highest intensity was taken to calculate the protein intensity.

Data Analysis

1) Comparison of Identification Results

The identified count of peptides and proteins of the results (proteome data set I) using peptide set I-optimized DIA, the results (proteome data set II) using peptide set II-optimized DIA and the results (triple repetitions) using undepleted-optimized DIA was compared.

Figure 4A:
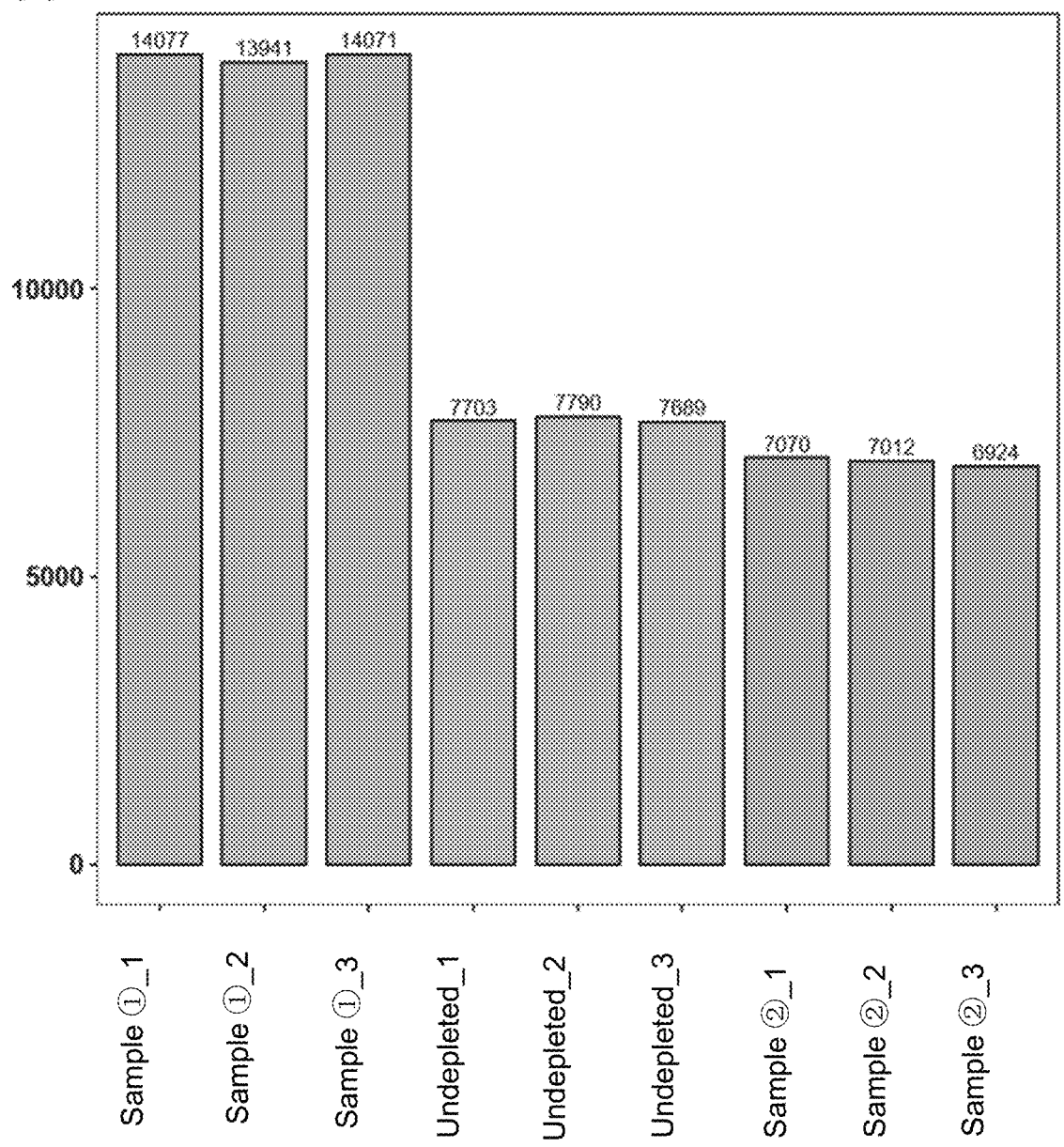
FIG. 4A and FIG. 4B illustrate a statistical diagram of a count of polypeptides (FIG. 4A) and a statistical diagram of a count of proteins (FIG. 4B) obtained by performing proteome analysis using an optimized DIA technique according to some embodiments of the present disclosure; wherein undepleted represents digested peptides of an original plasma sample of which HAPs are not removed; sample ① represents a use of a peptide set I; and sample ② represents a use of a peptide set II.
Figure 4B:
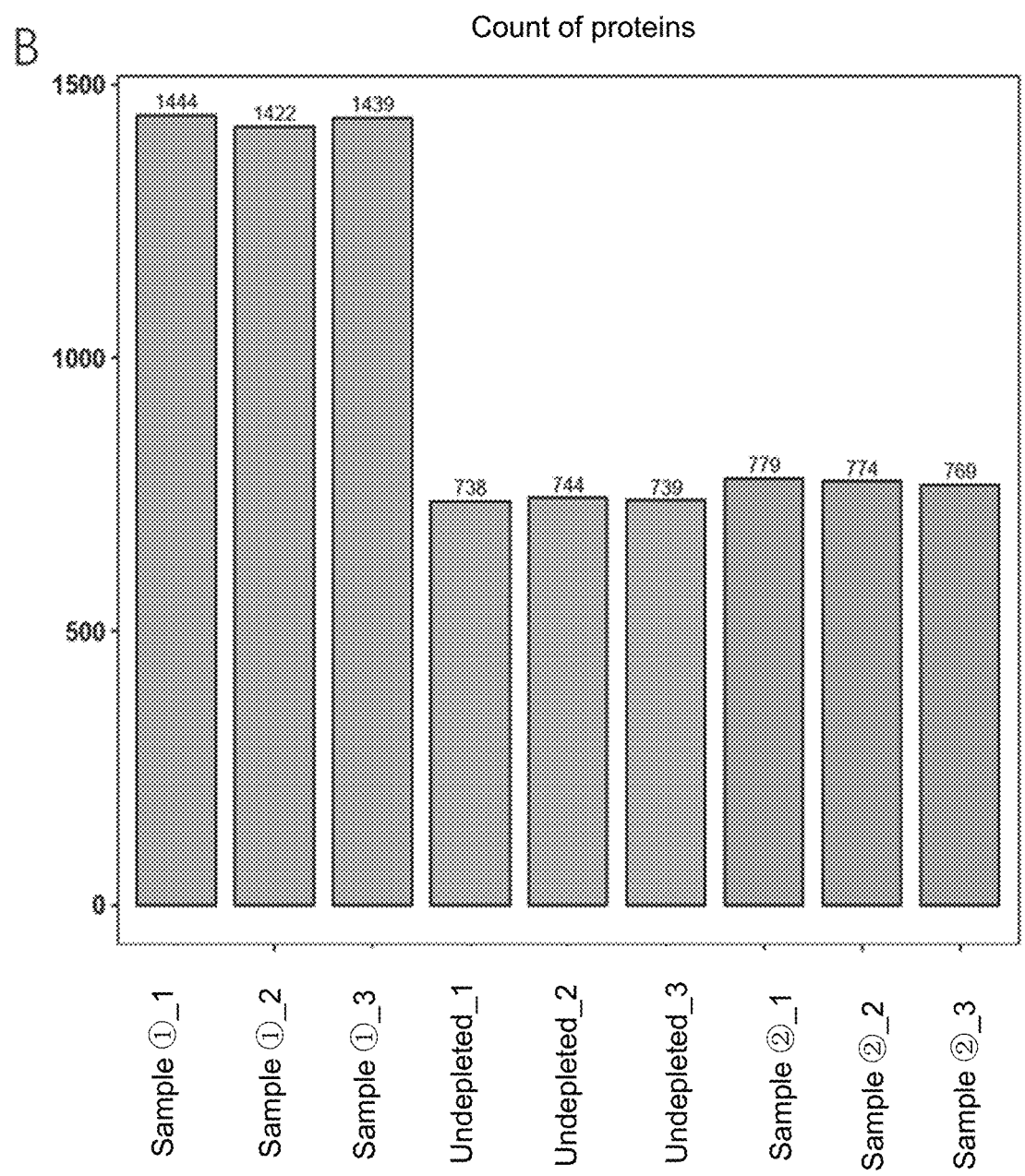

The identification results were shown in FIG. 4A and FIG. 4B. The highest count of polypeptides and proteins, with an average of 14,000 polypeptides and 1,400 proteins identified per repetition, was identified using the proteome data set I. 700 polypeptides and 770 proteins were identified using the proteome data set II. 7700 polypeptides and 740 proteins were identified using the results of Undepleted-optimized DIA.

Figure 5A:
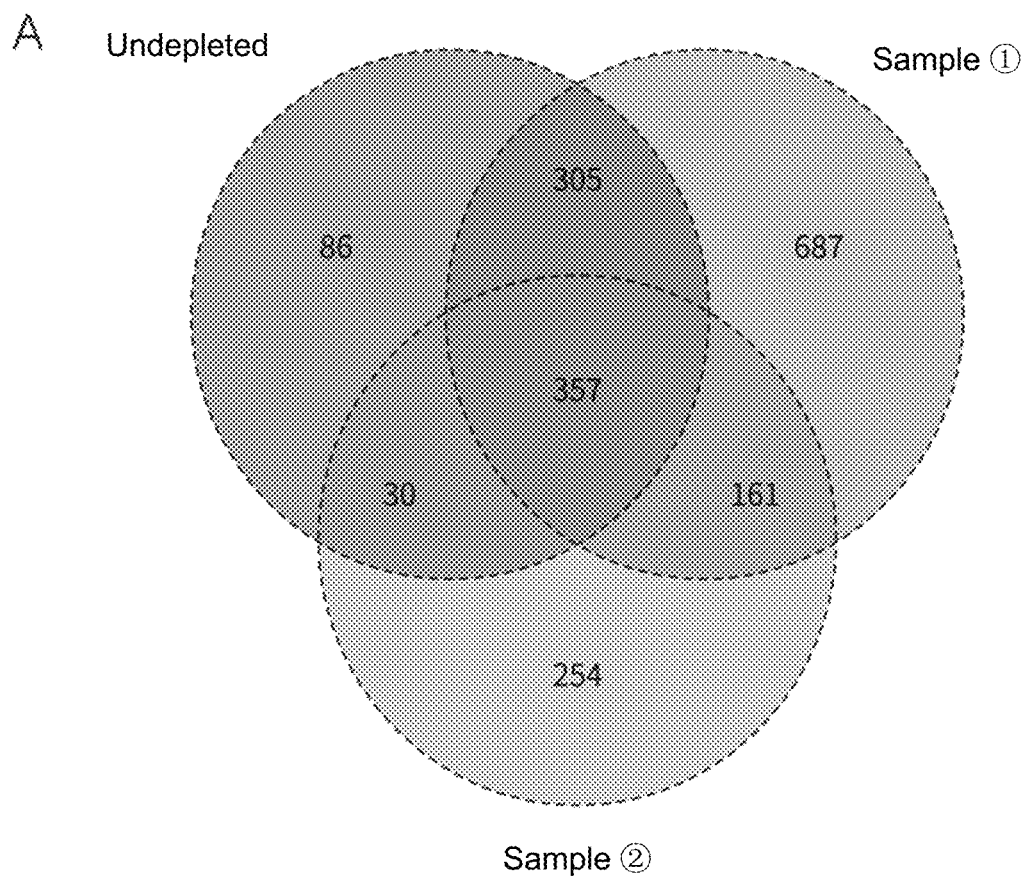
FIG. 5A and FIG. 5B illustrate a Venn diagram (FIG. 5A) of proteins and a distribution diagram (FIG. 5B) of protein molecular weights obtained by performing proteome analysis using an optimized DIA technique according to some embodiments of the present disclosure; wherein undepleted represents digested peptides of an original plasma sample of which HAPs are not removed; sample ① represents a use of a peptide set I; and sample ② represents a use of a peptide set II.
Figure 5B:
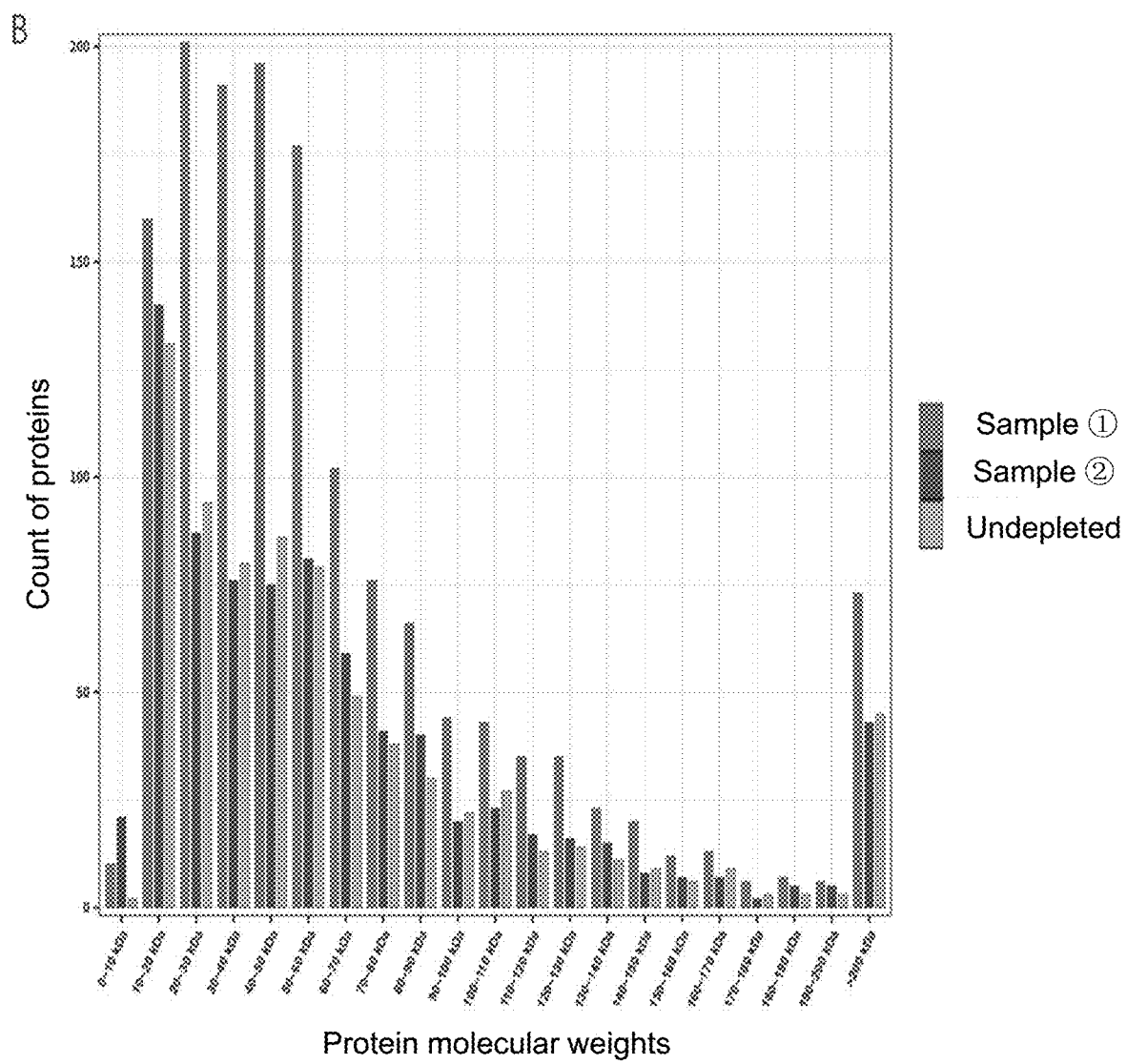

As shown in FIG. 5A, the proteome data set I and the proteome data set II basically contained all the proteins in the results of undepleted-optimized DIA, indicating that the removal based on the affinity technique and the removal based on the chemical precipitation are strongly complementary. Therefore, the results of undepleted-optimized DIA were discarded in the subsequent analysis in consideration of the simplicity of the method and the flux of the analysis. As shown in FIG. 5B, the chemical precipitation (proteome data set II) covered many low-molecular-weight proteins within a range of 1-20 kD, further showing the complementarity of the removal based on the affinity technique and the removal based on the chemical precipitation.

2) Analysis on Quantitative Reproducibility and Proteome Coverage of Removal of HAPs The reproducibility of removing the HAPs is an important factor in evaluating the feasibility of the method for analyzing the body fluid proteome for deep coverage of plasma proteome. Five repetitions were performed to examine the reproducibility of the method for analyzing the body fluid proteome of the present disclosure.

Figure 6:
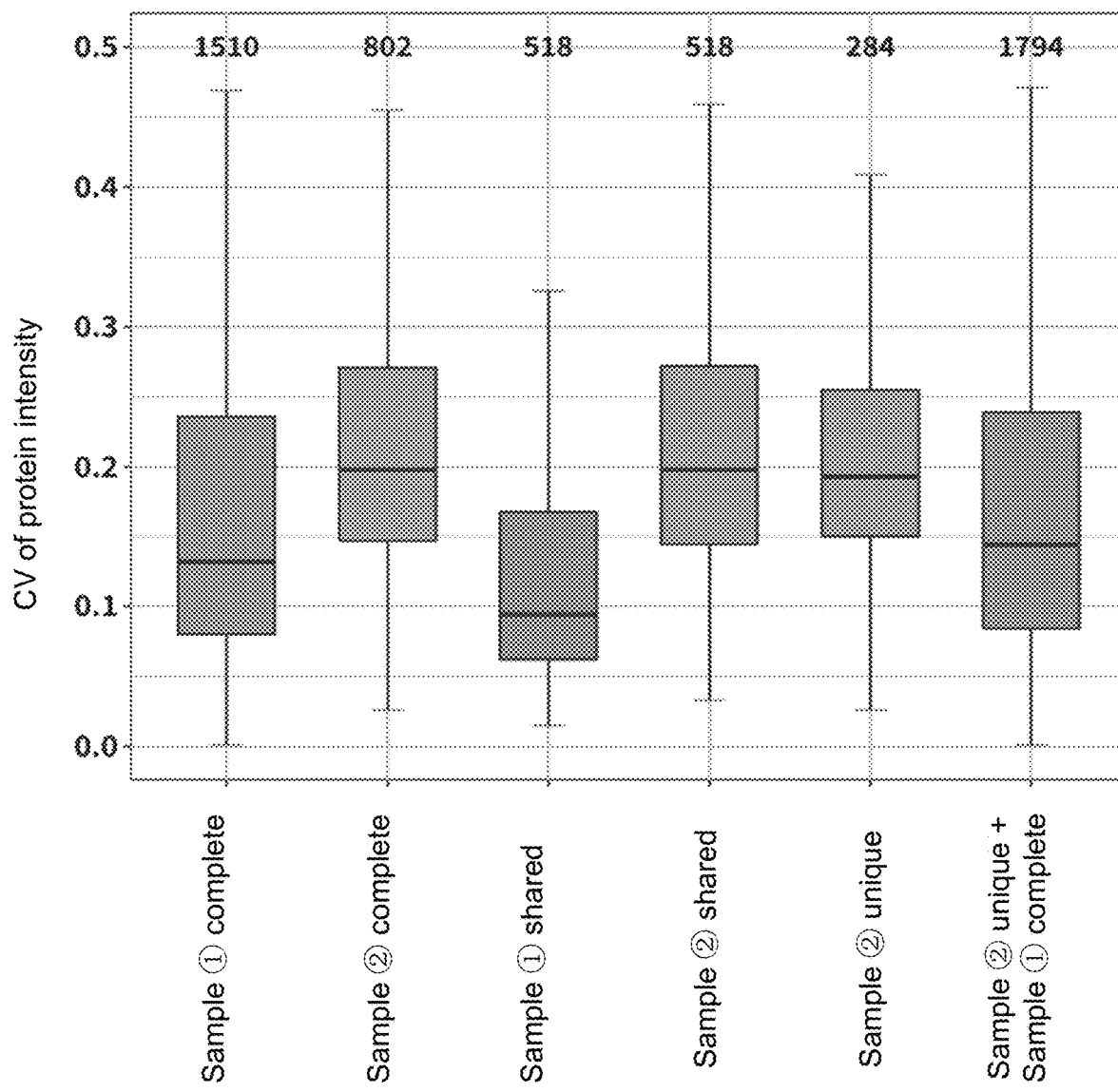
FIG. 6 illustrates a CV distribution diagram of protein intensity obtained by performing proteome analysis using an optimized DIA technique according to some embodiments of the present disclosure; wherein "sample ① complete" represents a CV distribution of protein intensity of all proteins identified by using peptide set I-optimized DIA; "sample ② complete" represents a CV distribution of protein intensity of all proteins identified by using peptide set II-optimized DIA; "sample ① shared" represents a CV distribution of protein intensity of proteins in peptide set I-optimized DIA which are jointly identified by peptide set I-optimized DIA and peptide set II-optimized DIA; "sample ② shared" represents a CV distribution of protein intensity of proteins in peptide set II-optimized DIA jointly identified by peptide set I-optimized DIA and peptide set II-optimized DIA; "sample ② unique" represents a CV distribution of protein intensity of unique proteins identified by peptide set II-optimized DIA; and "sample ① complete+sample ② unique" represents a CV distribution of protein intensity of all proteins identified by peptide set I-optimized DIA and unique proteins identified by peptide set II-optimized DIA.

As shown in FIG. 6, with five repetitions, 1,510 proteins were quantified in the proteome data set I, and a median RSD of the quantitative protein intensity was 13%, showing the good reproducibility of the affinity technique. 802 proteins were quantified in the proteome data set II, and the median RSD of the quantitative protein intensity was 20%, showing the good quantitative reproducibility of the chemical precipitation method. 992 proteins were uniquely quantified in the proteome data set I, which could only be attributed to the affinity technique; 284 proteins were uniquely quantified in the proteome data set II, which could only be attributed to the chemical precipitation.

Then the reproducibility of the 518 proteins quantified both in the proteome data set I and the proteome data set II was compared, showing that the reproducibility in the HAPs removal based on the affinity technique was better than the reproducibility in HAPs removal based on the chemical precipitation. Thus the 518 proteins were quantified in the proteome data set I.

Therefore, a collection of all the protein data sets quantified in the proteome data set I and the protein data sets quantified uniquely in the proteome data set II was taken as the final quantified proteome data set obtained by the method for analyzing the body fluid proteome of the present disclosure. The data set contained a total of 1,794 proteins, and the median RSD of the protein intensity was 14%, showing that the method for analyzing the body fluid proteome of the present disclosure has good reproducibility.

3) Coverage Analysis on the Final Quantified Proteome Data Set

Figure 7A:
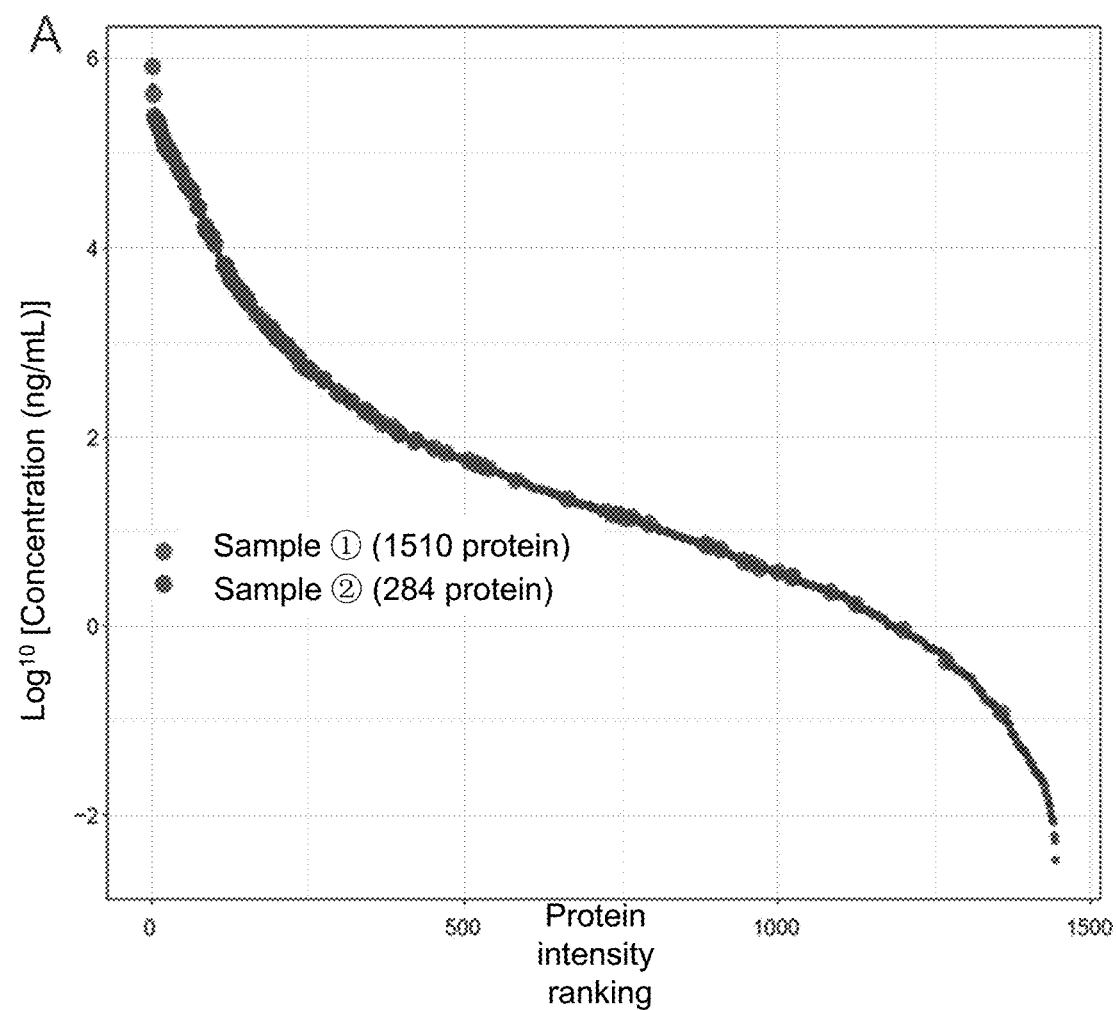
Figure 7B:
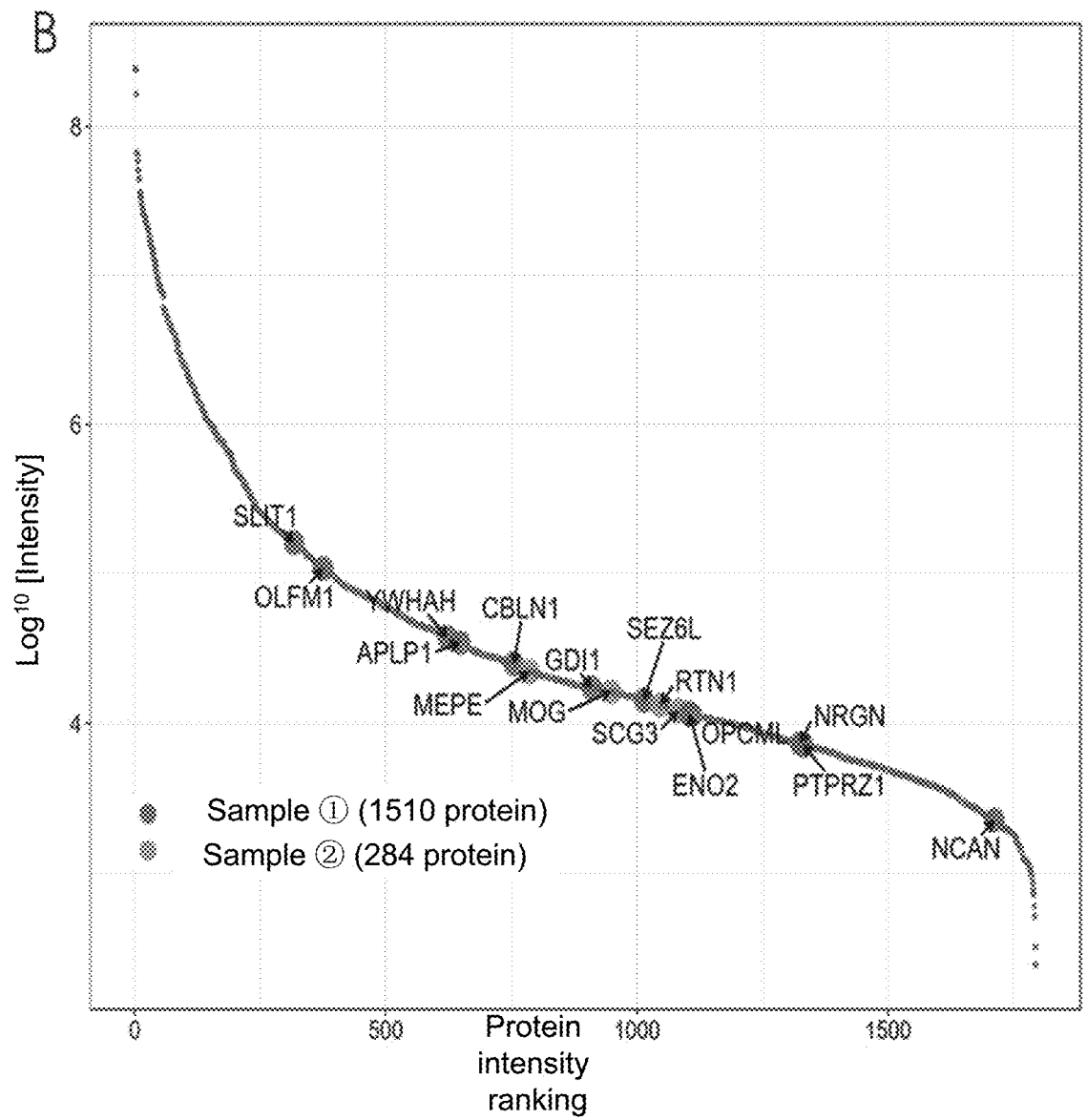
Figure 7C:
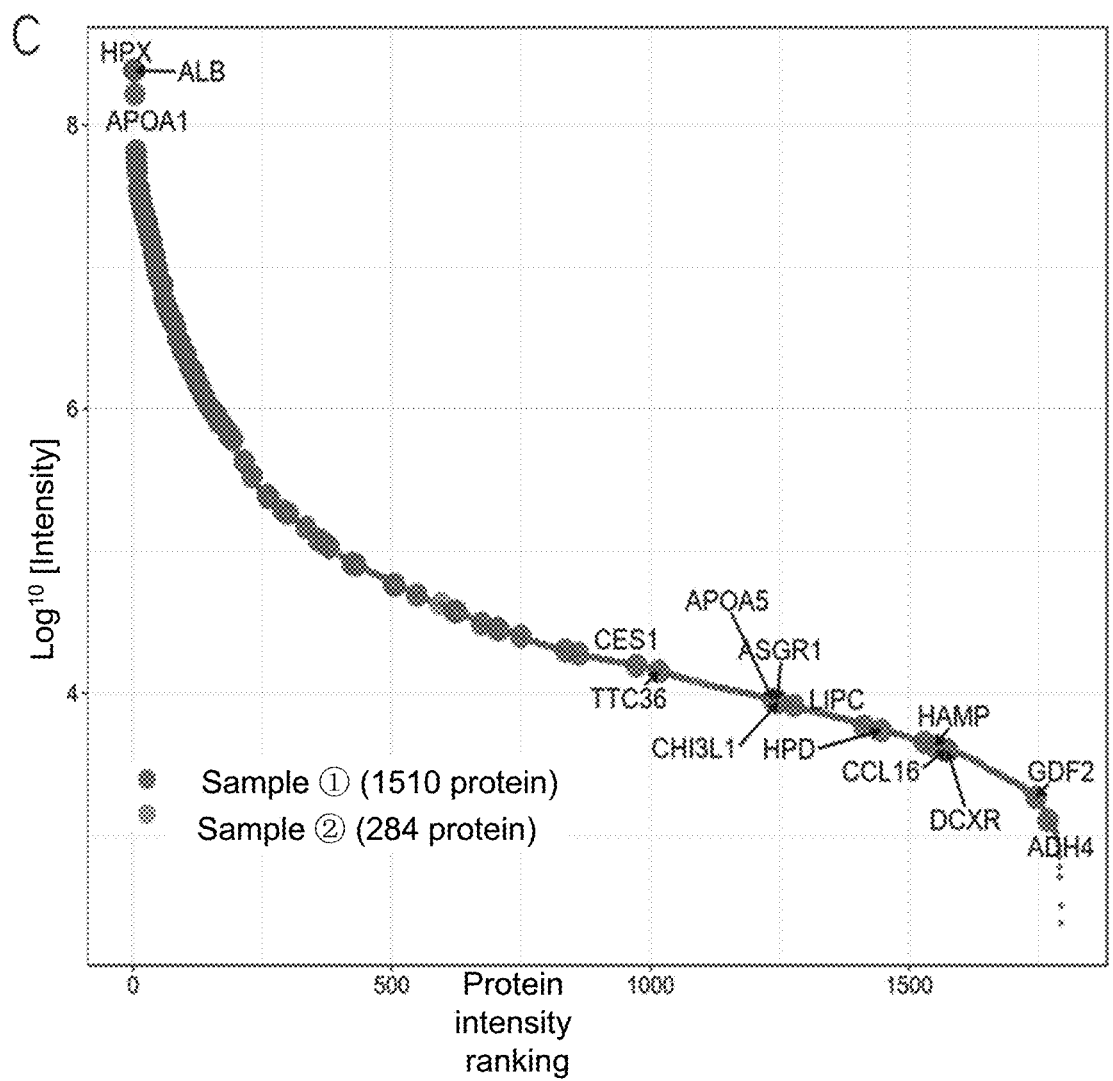

The quantified 1794 proteins achieved deep coverage of the plasma proteome. These 1794 proteins covered a dynamic range of 8 orders of magnitude, including many clinically significant proteins. 114 of the 222 FDA-approved biomarkers were covered (FDA-approved biomarkers can be downloaded at http://mrmasaydb.proteincentre.com/) (FIG. 7A, Table 2). 16 proteins were brain tissue-specific proteins in Human Tissue Proteome Atlas (https://www.proteinatlas.org/humanproteome/tissue) (FIG. 7B, Table 3); 124 proteins were liver tissue-specific proteins in Human Tissue Proteome Atlas (https://www.proteinatlas.org/humanproteome/tissue) (FIG. 7C, Table 4).

TABLE 2

FDA-approved biomarkers covered by the final quantified proteome data set in the body fluid sample

| No. | Protein No. | Gene | Protein description |
|---|---|---|---|
| 1 | P00450 | CP | ceruloplasmin |
| 2 | P02753 | RBP4 | Retinol binding protein 4 (RBP) |
| 3 | P01024 | C3 | Complement C3 |
| 4 | P02790 | HPX | Hemopexin |
| 5 | P02647 | APOA1 | Apolipoprotein A-I |
| 6 | P01023 | A2M | α-2-macroglobulin |
| 7 | P01008 | SERPINC1 | Antithrombin-III |
| 8 | P01009 | SERPINA1 | α-1-antitrypsin |
| 9 | P02766 | TTR | Transthyxine protein |
| 10 | P02671 | FGA | α-chain fibrinogen |
| 11 | P02765 | AHSG | α-2-HS-glycoprotein |
| 12 | P00738 | HP | Haptoglobin |
| 13 | P02763 | ORM1 | α-1-acidic glycoprotein 1 |
| 14 | P02675 | FGB | β-chain fibrinogen |
| 15 | P02787 | TF | Serum transferrin |
| 16 | P08697 | SERPINF2 | α-2-antiplasmin |
| 17 | P01019 | AGT | Hypertensin precursor |
| 18 | P0C0L4 | C4A | Complement C4-A |
| 19 | P0C0L5 | C4B | Complement C4-B |
| 20 | P04114 | APOB | Apolipoprotein B-100 |
| 21 | P02760 | AMBP | Protein AMBP |
| 22 | P02649 | APOE | Apolipoprotein E |
| 23 | P19652 | ORM2 | α-1-acidic glycoprotein 2 |
| 24 | P02751 | FN1 | Fibronectin |
| 25 | P01031 | C5 | Complement C5 |
| 26 | P02749 | APOH | β-2-glycoprotein 1 |
| 27 | P00734 | F2 | Prothrombin |
| 28 | P00747 | PLG | Profibrinolysin |
| 29 | P05155 | SERPING1 | Plasma protease C1 inhibitor |
| 30 | P07478 | PRSS2 | Trypsin-2 |
| 31 | P07477 | PRSS1 | Trypsin-1 |
| 32 | P69905 | HBA1 | Hemoglobin subunit-α |
| 33 | P00742 | F10 | Blood coagulation factor X |
| 34 | P04278 | SHBG | Sex hormone binding globulin |
| 35 | P68871 | HBB | Hemoglobin subunit β |
| 36 | P06276 | BCHE | Cholinesterase |
| 37 | P12259 | F5 | Blood coagulation factor V |
| 38 | P00740 | F9 | Blood coagulation factor IX |
| 39 | P00748 | F12 | Blood coagulation factor XII |
| 40 | P04275 | VWF | Vascular Willebrand factor |
| 41 | P04070 | PROC | Vitamin K-dependent protein C |
| 42 | P17936 | IGFBP3 | Insulin-like growth factor-binding protein 3 |
| 43 | P02741 | CRP | C-reactive protein |
| 44 | P03952 | KLKB1 | Plasma kallikrein |
| 45 | P02746 | C1QB | Complement C1q subunit B |
| 46 | P03951 | F11 | Blood coagulation factor XI |
| 47 | P01034 | CST3 | Cystatin-C |
| 48 | P02775 | PPBP | Platelet basic protein |
| 49 | P07225 | PROS1 | Vitamin K-dependent protein S |
| 50 | P05160 | F13B | Coagulation factor XIII B-chain |
| 51 | P61769 | B2M | β2-microglobulin |
| 52 | P08519 | LPA | apolipoprotein (a) |
| 53 | P43251 | BTD | Biotinidase |
| 54 | P61626 | LYZ | lysozyme C |
| 55 | P07359 | GP1BA | Platelet glycoprotein Ib α-chains |
| 56 | P01344 | IGF2 | Insulin-like growth factor II |
| 57 | P08709 | F7 | Blood coagulation factor VII |
| 58 | P06702 | S100A9 | Protein S100-A9 |
| 59 | P00488 | F13A1 | coagulation factor XIII A chain |
| 60 | P02747 | C1QC | Complement C1q, the subunit C |
| 61 | P04075 | ALDOA | Fructose diphosphate aldolase A |
| 62 | P02745 | C1QA | Complement C1q, subunit A |
| 63 | P08514 | ITGA2B | Integrin α-IIb |
| 64 | P04040 | CAT | Catalase |
| 65 | P05062 | ALDOB | Fructose diphosphate aldolase B |
| 66 | P07195 | LDHB | L-lactate dehydrogenase B chain |
| 67 | P05106 | ITGB3 | Integrin-based β -3 |
| 68 | P02788 | LTF | Lactotransferrin |
| 69 | P14618 | PKM | Pyruvate kinase PKM |
| 70 | P05556 | ITGB1 | Integrin-based β -1 |
| 71 | P05109 | S100A8 | Protein S100-A8 |
| 72 | P35030 | PRSS3 | Trypsin-3 |
| 73 | P05019 | IGF1 | Insulin-like growth factor I |
| 74 | P40197 | GP5 | Platelet glycoprotein V |
| 75 | P00338 | LDHA | L-lactate dehydrogenase A chain |
| 76 | P09972 | ALDOC | Fructose diphosphate aldolase C |
| 77 | P02792 | FTL | Ferroprotein light chain |
| 78 | P06732 | CKM | Creatine kinase type M |
| 79 | P02144 | MB | myoglobin |
| 80 | Q13093 | PLA2G7 | Platelet-activating factor acetylhydrolase |
| 81 | P06744 | GPI | Glucose-6-beta-phosphate isomerase |
| 82 | P17174 | GOT1 | Cytoplasmic aspartate aminotransferase |
| 83 | P13224 | GP1BB | Platelet glycoprotein Ib β-chains |
| 84 | P00390 | GSR | Mitochondrial glutathione reductase |
| 85 | P16671 | CD36 | Platelet glycoprotein 4 |
| 86 | P12821 | ACE | Angiotensin-Converting |
| 87 | P04746 | AMY2A | Pancreatic a-amylase |
| 88 | P14770 | GP9 | Platelet glycoprotein IX |
| 89 | P14780 | MMP9 | Matrix metalloproteinase-9 |
| 90 | P48735 | IDH2 | Mitochondrial isocitrate dehydrogenase [NADP] |
| 91 | P12277 | CKB | Creatine kinase type B |
| 92 | P17301 | ITGA2 | Integrin α-2 |
| 93 | P09619 | PDGFRB | Platelet-derived growth factor receptor B |
| 94 | P08833 | IGFBP1 | Insulin-like growth factor-binding protein 1 |
| 95 | O75874 | IDH1 | Cytosolic isocitrate dehydrogenase [NADP] |
| 96 | P05164 | MPO | myeloperoxidase |
| 97 | P24298 | GPT | Alanine aminotransferase 1 |
| 98 | P02786 | TFRC | Transferrin receptor protein 1 |
| 99 | P05121 | SERPINE1 | Plasminogen activator inhibitor 1 |
| 100 | P11413 | G6PD | Glucose-6-phosphate-1-dehydrogenase |
| 101 | P05186 | ALPL | Alkaline phosphatase, tissue nonspecific isoenzymes |
| 102 | P00505 | GOT2 | Mitochondrial aspartate aminotransferase |
| 103 | P00451 | F8 | Coagulation factor VIII |
| 104 | P15941 | MUC1 | mucoprotein-1 |
| 105 | P19440 | GGT1 | Glutathione hydrolase 1 zymogen |
| 106 | P28838 | LAP3 | Cytoplasmin |
| 107 | P24666 | ACP1 | Low-molecular-weight phosphotyrosine protein phosphatase |
| 108 | P20061 | TCN1 | Transcobalamin-1 |
| 109 | P01236 | PRL | Mammotropic hormone |
| 110 | P17931 | LGALS3 | Galectin-3 |
| 111 | P21980 | TGM2 | Protein-glutamine γ -glutamyltransferase 2 |
| 112 | P06280 | GLA | α-Galactosidase A |
| 113 | Q00796 | SORD | SDH |
| 114 | P24158 | PRTN3 | Myeloblastin |

TABLE 3

Brain tissue specific proteins in Human Tissue Proteome Atlas covered by the final quantified proteome data set in the body fluid sample

| No. | Protein No. | Gene | Protein description |
|---|---|---|---|
| 1 | O75093 | SLIT1 | Slit guidance ligand 1 |
| 2 | Q99784 | OLFM1 | Olfactory pheromone 1 |
| 3 | Q04917 | YWHAH | Tyrosine 3-monooxygenase/tryptophan 5-monooxygenase-activated protein η |
| 4 | P51693 | APLP1 | Amyloid β precursor-like protein 1 |
| 5 | P23435 | CBLN1 | Cerebellar protein 1 precursor |
| 6 | Q9NQ76 | MEPE | Matrix extracellular phosphoglycoproteins |
| 7 | P31150 | GDI1 | GDP dissociation inhibitor 1 |
| 8 | Q16653 | MOG | Myelin sheath oligodendrocyte glycoproteins |
| 9 | Q9BYH1 | SEZ6L | Seizure-related 6 homolog-like protein |
| 10 | Q16799 | RTN1 | reticuloendothelin 1 |
| 11 | Q8WXD2 | SCG3 | Secreted granin III |
| 12 | P09104 | ENO2 | Enolase 2 |
| 13 | Q14982 | OPCML | Opioid-binding protein/cell-adhesion molecule-like protein |
| 14 | Q92686 | NRGN | Neuroparticle protein |
| 15 | P23471 | PTPRZ1 | Protein tyrosine phosphatase receptor type Z1 |
| 16 | O14594 | NCAN | Neurocan |

TABLE 4

Liver tissue pecific proteins in Human Tissue Proteome Atlas covered by the final quantified proteome data set in the body fluid sample

| No. | Protein No. | Gene | Protein description |
|---|---|---|---|
| 1 | P02790 | HPX | Hemopexin |
| 2 | P02768 | ALB | Albumin |
| 3 | P02647 | APOA1 | Apolipoprotein A1 |
| 4 | P01024 | C3 | Complementary C3 |
| 5 | P01011 | SERPINA3 | Serine protease inhibitor family A member 3 |
| 6 | P02765 | AHSG | α2-HS glycoprotein |
| 7 | P02774 | GC | GC, a vitamin D-binding protein |
| 8 | P02652 | APOA2 | Apolipoprotein A2 |
| 9 | P04004 | VTN | Vitronectin |
| 10 | P01042 | KNG1 | Kininogen-1 |
| 11 | P04217 | A1BG | α-1-B glycoprotein |
| 12 | P00734 | F2 | coagulation factor II, thrombin |
| 13 | Q14624 | ITIH4 | α-trypsin inhibitor heavy chain family member 4 |
| 14 | P02749 | APOH | apolipoprotein H |
| 15 | P19823 | ITIH2 | α-trypsin inhibitor heavy chain 2 |
| 16 | P02760 | AMBP | α-1-microglobulin/uropancreatic pancreas, enzymlogin precursor |
| 17 | P00450 | CF | ceruloplasmin |
| 18 | P02656 | APOC3 | Apolipoprotein C3 |
| 19 | P01008 | SERPINC1 | Serine protease inhibitor family C member 1 |
| 20 | P05155 | SERPING1 | Serine protease inhibitor family G member 1 |
| 21 | P00747 | PLG | Profibrinolysin |
| 22 | P02753 | RBP4 | Retinol-binding protein 4 |
| 23 | P08603 | CFH | Complement factor H |
| 24 | P00751 | CFB | Complement factor B |
| 25 | P02654 | APOC1 | Apolipoprotein C1 |
| 26 | P04003 | C4BPA | Complement component 4-binding protein a |
| 27 | P19827 | ITIH1 | α-trypsin inhibitor heavy chain 1 |
| 28 | P08697 | SERPINF2 | Serine protease inhibitor family F member 2 |
| 29 | P05546 | SERPIND1 | Serine protease inhibitor family D member 1 |
| 30 | P43652 | AFM | Afarin |
| 31 | P04196 | HRG | Histidine-rich glycoproteins |
| 32 | P01019 | AGT | Hypertensin precursor |
| 33 | P02748 | C9 | Complementary C9 |
| 34 | P02655 | APOC2 | Apolipoprotein C2 |
| 35 | P03952 | KLKB1 | Mallikrein B1 |
| 36 | P08185 | SERPINA6 | Serine protease inhibitor family A member 6 |
| 37 | P02750 | LRG1 | Leucine-rich α-2-glycoprotein 1 |
| 38 | P01031 | C5 | Complementary C5 |
| 39 | Q96PD5 | PGLYRP2 | Peptidoglycan recognition protein 2 |
| 40 | Q03591 | CFHR1 | Complement factor H-associated protein 1 |
| 41 | P13671 | C6 | Complementary C6 |
| 42 | O95445 | APOM | Apolipoprotein M |
| 43 | P22792 | CPN2 | Carboxypeptidase N subunit 2 |
| 44 | P01009 | SERPINA1 | Serine protease inhibitor family A member 1 |
| 45 | P35858 | IGFALS | Insulin-like growth factor binding protein unstable subunits |
| 46 | P35542 | SAA4 | Serum amyloid protein A4, constitutively |
| 47 | P02787 | TF | Transferrin |
| 48 | P20851 | C4BPB | Complement component 4-binding protein β |
| 49 | P27169 | PON1 | Paraoxonase 1 |
| 50 | Q06033 | ITIH3 | Trypsin inhibitor heavy chain 3 |
| 51 | P00748 | F12 | blood coagulation factor XII |
| 52 | Q14520 | HABP2 | Hyaluronan-binding protein 2 |
| 53 | P00742 | F10 | blood coagulation factor X |
| 54 | P07358 | C8B | Complement C8 β chain |
| 55 | P06681 | C2 | Complementary C2 |
| 56 | P07360 | C8G | Complement C8 γ chain |
| 57 | Q96IY4 | CPB2 | Carboxypeptidase B2 |
| 58 | P02743 | APCS | Serum amyloid P fraction |
| 59 | P05543 | SERPINA7 | Member of the serine protease inhibitor family A 7 |
| 60 | P07357 | C8A | Complement C8 a chain |
| 61 | P80108 | GPLD1 | Glycosylphosphatidylinositol-specific phospholipase D1 |
| 62 | P15169 | CPN1 | Carboxypeptidase N subunit 1 |
| 63 | Q02985 | CFHR3 | Complement factor H-associated protein 3 |
| 64 | P06276 | BCHE | Butyryl cholinesterase (BUCHE) |
| 65 | P02671 | FGA | α -chain fibrinogen |
| 66 | P26927 | MST1 | # Not applicable |
| 67 | P55056 | APOC4 | Apolipoprotein C4 |
| 68 | P01344 | IGF2 | Insulin-like growth factor 2 |
| 69 | P00740 | F9 | Blood coagulation factor IX |
| 70 | P00738 | HP | Haptoglobin |
| 71 | P08519 | LPA | Lipoprotein (a) |
| 72 | P05160 | F13B | Coagulation factor XIII B-chain |
| 73 | Q04756 | HGFAC | HGF activator |
| 74 | P03951 | F11 | Blood coagulation factor XI |
| 75 | P20742 | PZP | PZP, a α -2-macroglobulin-like form |
| 76 | P19652 | ORM2 | Oral mucin 2 |
| 77 | P36980 | CFHR2 | Complement factor H-associated protein 2 |
| 78 | P02679 | FGG | γ-chain fibrinogen |
| 79 | Q9UK55 | SERPINA10 | Serine protease inhibitor family A member 10 |
| 80 | P11226 | MBL2 | Mannose-binding lectin 2 |
| 81 | P02675 | FGB | β-chain fibrinogen |
| 82 | Q9UGM5 | FETUB | Fetuin B |
| 83 | P02763 | ORM1 | Oral mucin 1 |
| 84 | P22891 | PROZ | Protein Z, a vitamin K-dependent plasma glycoprotein |
| 85 | O00187 | MASP2 | Mannnitol binds lectin serine peptidase 2 |

TABLE 4-continued

Liver tissue pecific proteins in Human Tissue Proteome Atlas covered by the final quantified proteome data set in the body fluid sample

| No. | Protein No. | Gene | Protein description |
|---|---|---|---|
| 86 | P04070 | PROC | Protein C, the inactivation agent of the coagulation factors Va and VIIIa |
| 87 | P18428 | LBP | Lipopolysaccharide binding protein |
| 88 | Q13790 | APOF | Apolipoprotein F |
| 89 | P02741 | CRP | C reactive protein |
| 90 | Q9BXR6 | CFHR5 | Complement factor H correlation 5 |
| 91 | Q92496 | CFHR4 | Complement factor H correlation 4 |
| 92 | Q13103 | SPP2 | Secretory phosphoprotein 2 |
| 93 | P08709 | F7 | blood coagulation factor VII |
| 94 | Q9Y6Z7 | COLEC10 | Member of the lectin subfamily 10 |
| 95 | Q15485 | FCN2 | Fikelin 2 |
| 96 | Q76LX8 | ADAMTS13 | ADAM with platelet reactive protein type 1 motif 13, metalopeptidase |
| 97 | P55103 | INHBC | Arrestin β C subunit |
| 98 | Q86U17 | SERPINA11 | Serine protease inhibitor family A member 11 |
| 99 | Q15166 | PON3 | Paraoxonase 3 |
| 100 | P03950 | ANG | Angiogenin |
| 101 | Q8WWZ8 | OIT3 | Oncoprotein-inducible transcript 3 |
| 102 | Q969E1 | LEAP2 | Liver enrichment enriched antimicrobial peptides 2 |
| 103 | P00739 | HPR | Binding globin-associated proteins |
| 104 | P07307 | ASGR2 | Dessialate glycoprotein receptor 2 |
| 105 | PODJI9 | SAA2 | Serum amyloid protein A2 |
| 106 | Q08830 | FGL1 | Fibrinogen-like 1 |
| 107 | Q9Y5C1 | ANGPTL3 | Angiogenin-like 3 |
| 108 | O14960 | LECT2 | Leukocyte-derived chemokine 2 |
| 109 | Q8NI99 | ANGPTL6 | Angiogenin-like 6 |
| 110 | P34096 | RNASE4 | Ribonuclease A family member 4 |
| 111 | P23141 | CES1 | Carboxylate enzyme 1 |
| 112 | A6NLP5 | TTC36 | Tetrapeptide repeat domain 36 |
| 113 | Q6Q788 | APOA5 | Apolipoprotein A5 |
| 114 | P07306 | ASGR1 | Dessialate glycoprotein receptor 1 |
| 115 | P36222 | CHI3L1 | Chitinase 3-like 1 |
| 116 | P11150 | LIPC | Hepatic-type lipase C |
| 117 | P58166 | INHBE | Arrestin βE subunit |
| 118 | P32754 | HPD | 4-hydroxyphenylpyruvate dioxygenase |
| 119 | Q9UBQ7 | GRHPR | Glyoxylate and hydroxypyruvate reductase |
| 120 | P81172 | HAMP | Iron modulin antimicrobial peptide |
| 121 | O15467 | CCL16 | C-C motif chemokine ligand 16 |
| 122 | Q7Z4W1 | DCXR | Diyl and L-cellulose reductase |
| 123 | Q9UK05 | GDF2 | Growth and differentiation factor 2 |
| 124 | P08319 | ADH4 | Ethanol dehydrogenase 4 (class II), pi-polypeptide |

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These modifications, improvements, and amendments are intended to be suggested by the present disclosure, and are within the spirit and scope of the exemplary embodiments of the present disclosure.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for analyzing a body fluid proteome, comprising:
obtaining a peptide set I enriched with low-abundant proteins (LAPs) by removing high-abundant proteins (HAPs) in an initial sample A using an affinity technique that utilizes antibodies to the HAPs as affinity ligands;
obtaining a peptide set II enriched with LAPs by removing HAPs in an initial sample B using chemical precipitation, wherein the initial sample A and the initial sample B are obtained from a same body fluid sample of a same subject;
constructing a plasma proteome spectrum library based on the peptide set I and the peptide set II;
obtaining a proteome data set I and a proteome data set II by performing proteomic analysis on the peptide set I and the peptide set II by using an optimized data independent acquisition (DIA) technique; wherein the proteomic analysis includes analyzing deep coverage plasma spectrums corresponding to the peptide set I and the peptide set II in the plasma proteome spectrum library; and
determining a final quantified proteome data set of the body fluid sample based on the proteome data set I and the proteome data set II;
wherein the determining a final quantified proteome data set of the body fluid sample based on the proteome data set I and the proteome data set II includes:
obtaining a proteome data set III by removing overlapping data of the proteome data set II with the proteome data set I from the proteome data set II; and
using the proteome data set I and the proteome data set III as the final quantified proteome data set of the body fluid sample, wherein the final quantified proteome data set consists of whole data of data set I and data in data set II that does not contain the overlapping data, and the final quantified proteome data set includes biomarkers listed in Table 2:

TABLE 2

| No. | Protein No. | Gene | Protein description |
|---|---|---|---|
| 1 | P00450 | CP | ceruloplasmin |
| 2 | P02753 | RBP4 | Retinol binding protein 4 (RBP) |
| 3 | P01024 | C3 | Complement C3 |
| 4 | P02790 | HPX | Hemopexin |
| 5 | P02647 | APOA1 | Apolipoprotein A-I |
| 6 | P01023 | A2M | α-2-macroglobulin |
| 7 | P01008 | SERPINC1 | Antithrombin-III |

TABLE 2-continued

| No. | Protein No. | Gene | Protein description |
|---|---|---|---|
| 8 | P01009 | SERPINA1 | α-1-antitrypsin |
| 9 | P02766 | TTR | Transthyxine protein |
| 10 | P02671 | FGA | α-chain fibrinogen |
| 11 | P02765 | AHSG | α-2-HS-glycoprotein |
| 12 | P00738 | HP | Haptoglobin |
| 13 | P02763 | ORM1 | α-1-acidic glycoprotein 1 |
| 14 | P02675 | FGB | β-chain fibrinogen |
| 15 | P02787 | TF | Serum transferrin |
| 16 | P08697 | SERPINF2 | α-2-antiplasmin |
| 17 | P01019 | AGT | Hypertensin precursor |
| 18 | P0C0L4 | C4A | Complement C4-A |
| 19 | P0C0L5 | C4B | Complement C4-B |
| 20 | P04114 | APOB | Apolipoprotein B-100 |
| 21 | P02760 | AMBP | Protein AMBP |
| 22 | P02649 | APOE | Apolipoprotein E |
| 23 | P19652 | ORM2 | α-1-acidic glycoprotein 2 |
| 24 | P02751 | FN1 | Fibronectin |
| 25 | P01031 | C5 | Complement C5 |
| 26 | P02749 | APOH | β-2-glycoprotein 1 |
| 27 | P00734 | F2 | Prothrombin |
| 28 | P00747 | PLG | Profibrinolysin |
| 29 | P05155 | SERPING1 | Plasma protease C1 inhibitor |
| 30 | P07478 | PRSS2 | Trypsin-2 |
| 31 | P07477 | PRSS1 | Trypsin-1 |
| 32 | P69905 | HBA1 | Hemoglobin subunit-α |
| 33 | P00742 | F10 | Blood coagulation factor X |
| 34 | P04278 | SHBG | Sex hormone binding globulin |
| 35 | P68871 | HBB | Hemoglobin subunit β |
| 36 | P06276 | BCHE | Cholinesterase |
| 37 | P12259 | F5 | Blood coagulation factor V |
| 38 | P00740 | F9 | Blood coagulation factor IX |
| 39 | P00748 | F12 | Blood coagulation factor XII |
| 40 | P04275 | VWF | Vascular Willebrand factor |
| 41 | P04070 | PROC | Vitamin K-dependent protein C |
| 42 | P17936 | IGFBP3 | Insulin-like growth factor-binding protein 3 |
| 43 | P02741 | CRP | C-reactive protein |
| 44 | P03952 | KLKB1 | Plasma kallikrein |
| 45 | P02746 | C1QB | Complement C1q subunit B |
| 46 | P03951 | F11 | Blood coagulation factor XI |
| 47 | P01034 | CST3 | Cystatin-C |
| 48 | P02775 | PPBP | Platelet basic protein |
| 49 | P07225 | PROS1 | Vitamin K-dependent protein S |
| 50 | P05160 | F13B | Coagulation factor XIII B-chain |
| 51 | P61769 | B2M | β2-microglobulin |
| 52 | P08519 | LPA | apolipoprotein (a) |
| 53 | P43251 | BTD | Biotinidase |
| 54 | P61626 | LYZ | lysozyme C |
| 55 | P07359 | GP1BA | Platelet glycoprotein Ib α-chains |
| 56 | P01344 | IGF2 | Insulin-like growth factor II |
| 57 | P08709 | F7 | Blood coagulation factor VII |
| 58 | P06702 | S100A9 | Protein S100-A9 |
| 59 | P00488 | F13A1 | coagulation factor XIII A chain |
| 60 | P02747 | C1QC | Complement C1q, the subunit C |
| 61 | P04075 | ALDOA | Fructose diphosphate aldolase A |
| 62 | P02745 | C1QA | Complement C1q, subunit A |
| 63 | P08514 | ITGA2B | Integrin α-IIb |
| 64 | P04040 | CAT | Catalase |
| 65 | P05062 | ALDOB | Fructose diphosphate aldolase B |
| 66 | P07195 | LDHB | L-lactate dehydrogenase B chain |
| 67 | P05106 | ITGB3 | Integrin-based ß -3 |
| 68 | P02788 | LTF | Lactotransferrin |
| 69 | P14618 | PKM | Pyruvate kinase PKM |
| 70 | P05556 | ITGB1 | Integrin-based β -1 |
| 71 | P05109 | S100A8 | Protein S100-A8 |
| 72 | P35030 | PRSS3 | Trypsin-3 |
| 73 | P05019 | IGF1 | Insulin-like growth factor I |
| 74 | P40197 | GP5 | Platelet glycoprotein V |
| 75 | P00338 | LDHA | L-lactate dehydrogenase A chain |
| 76 | P09972 | ALDOC | Fructose diphosphate aldolase C |
| 77 | P02792 | FTL | Ferroprotein light chain |
| 78 | P06732 | CKM | Creatine kinase type M |
| 79 | P02144 | MB | myoglobin |
| 80 | Q13093 | PLA2G7 | Platelet-activating factor acetylhydrolase |
| 81 | P06744 | GPI | Glucose-6-beta-phosphate isomerase |
| 82 | P17174 | GOT1 | Cytoplasmic aspartate aminotransferase |
| 83 | P13224 | GP1BB | Platelet glycoprotein Ib β-chains |
| 84 | P00390 | GSR | Mitochondrial glutathione reductase |
| 85 | P16671 | CD36 | Platelet glycoprotein 4 |
| 86 | P12821 | ACE | Angiotensin-Converting |
| 87 | P04746 | AMY2A | Pancreatic α-amylase |
| 88 | P14770 | GP9 | Platelet glycoprotein IX |
| 89 | P14780 | MMP9 | Matrix metalloproteinase-9 |
| 90 | P48735 | IDH2 | Mitochondrial isocitrate dehydrogenase [NADP] |
| 91 | P12277 | CKB | Creatine kinase type B |
| 92 | P17301 | ITGA2 | Integrin α-2 |
| 93 | P09619 | PDGFRB | Platelet-derived growth factor receptor β |
| 94 | P08833 | IGFBP1 | Insulin-like growth factor-binding protein 1 |
| 95 | O75874 | IDH1 | Cytosolic isocitrate dehydrogenase [NADP] |
| 96 | P05164 | MPO | myeloperoxidase |
| 97 | P24298 | GPT | Alanine aminotransferase 1 |
| 98 | P02786 | TFRC | Transferrin receptor protein 1 |
| 99 | P05121 | SERPINE1 | Plasminogen activator inhibitor 1 |
| 100 | P11413 | G6PD | Glucose-6-phosphate-1-dehydrogenase |
| 101 | P05186 | ALPL | Alkaline phosphatase, tissue nonspecific isoenzymes |
| 102 | P00505 | GOT2 | Mitochondrial aspartate aminotransferase |
| 103 | P00451 | F8 | Coagulation factor VIII |
| 104 | P15941 | MUC1 | mucoprotein-1 |
| 105 | P19440 | GGT1 | Glutathione hydrolase 1 zymogen |
| 106 | P28838 | LAP3 | Cytoplasmin |
| 107 | P24666 | ACP1 | Low-molecular-weight phosphotyrosine protein phosphatase |
| 108 | P20061 | TCN1 | Transcobalamin-1 |
| 109 | P01236 | PRL | Mammotropic hormone |
| 110 | P17931 | LGALS3 | Galectin-3 |
| 111 | P21980 | TGM2 | Protein-glutamine γ -glutamyltransferase 2 |
| 112 | P06280 | GLA | α-Galactosidase A |
| 113 | Q00796 | SORD | SDH |
| 114 | P24158 | PRTN3 | Myeloblastin. |

2. The method of claim 1, wherein the body fluid sample includes one or more of a plasma sample, a serum sample, a urine sample, an interstitial fluid sample, an intrapleural fluid sample, an intraperitoneal fluid sample, a cerebrospinal fluid sample, a semen sample, and a vaginal fluid sample.

3. The method of claim 1, wherein the HAPs include one or more of albumin, IgA, IgD, IgE, IgG, IgM, α1-acid glycoprotein, α1-antitrypsin, α2-macroglobulin, apolipoprotein A1, fibrinogen, haptoglobin, transferrin, complement C3, apolipoprotein A-II, α-2-HS-glycoprotein, apolipoprotein C-III, α-1-antichymotrypsin, a vitamin D-binding protein, ceruloplasmin, complement C4-A, complement C1q, hemagglutinin, kininogen-1, synaptotagmin 5, histidine-rich glycoprotein, vitronectin, a complement factor H, a plasma protease C1 inhibitor, C4b binding protein, and fibronectin.

4. The method of claim 1, wherein the antibodies to the HAPs are immobilized on solid phase carriers.

5. The method of claim 4, wherein the solid phase carrier includes one or more of cellulose, polyacrylamide, polystyrene, polyethylene, polypropylene, cross-linked dextran, glass, silicone rubber, agarose gel, and a gel resin.

6. The method of claim 1, wherein at least one of the removing the HAPs in the initial sample A using the affinity technique or the removing the HAPs in the initial sample B using the chemical precipitation is carried out in a multi-cavity vessel.

7. The method of claim 1, wherein the removing the HAPs in the initial sample B using the chemical precipitation includes: precipitating the HAPs by using an organic solvent as a precipitating agent.

8. The method of claim 7, wherein the organic solvent includes one or more of methanol, ethanol, isopropanol, acetonitrile, chloroform, trichloroacetic acid, and trifluoroacetic acid.

9. The method of claim 7, wherein the removing the HAPs in the initial sample B using the chemical precipitation further includes: denaturing the HAPs using a denaturant before precipitating the HAPs by using the precipitating agent.

10. The method of claim 9, wherein the denaturant includes at least one of guanidine hydrochloride and urea.

11. The method of claim 1, wherein the peptide set I for proteomic analysis using the optimized DIA technique is obtained after a sample to be tested I is reduced, alkylated, digested, and desalted.

12. The method of claim 1, wherein the peptide set II for proteomic analysis using the optimized DIA technique is obtained after a sample to be tested II is desalted, reduced, alkylated and digested.

13. The method of claim 1, wherein
the optimized DIA technique uses a column length of 50 cm and a column gradient of 90 min, including:
separating the proteome data set I and the peptide set II respectively by using HPLC with the column gradient of 90 min; wherein
a mobile phase A is 0.1% formic acid in $H_2O$ and a mobile phase B is 0.1% formic acid in 80% ACN, and
the column gradient is 0-4 min, 3-6% of B; 4-83 min, 6-30% of B; 83-87 min, 30%-90% of B; 87-90 min, 90% of B.

14. The method of claim 13, wherein in the optimized DIA technique, an MS1 resolution is set to 60 K, an MS2 resolution is set to 30 K, and a precursor ion scanning range is set to m/z 350-1200 and split into 50 windows.

15. The method of claim 1, wherein the removing overlapping data of the proteome data set II with the proteome data set I from the proteome data set II includes:
obtaining the proteome data set III by comparing the proteome data set I with the proteome data set II through a Venn diagram, and removing the overlapping data of the proteome data set II with the proteome data set I from the proteome data set II.

16. The method of claim 1, wherein the overlapping data of the proteome data set II with the proteome data set I is overlapping protein data of the proteome data set II and the proteome data set I.

17. The method of claim 1, wherein the subject includes at least one of a human being and a non-human mammal.

18. The method of claim 1, wherein the final quantified proteome data set further includes biomarkers listed in Table 3:

TABLE 3

| No. | Protein No. | Gene | Protein description |
|---|---|---|---|
| 1 | O75093 | SLIT1 | Slit guidance ligand 1 |
| 2 | Q99784 | OLFM1 | Olfactory pheromone 1 |
| 3 | Q04917 | YWHAH | Tyrosine 3-monooxygenase/tryptophan 5-monooxygenase-activated protein η |
| 4 | P51693 | APLP1 | Amyloid β precursor-like protein 1 |
| 5 | P23435 | CBLN1 | Cerebellar protein 1 precursor |
| 6 | Q9NQ76 | MEPE | Matrix extracellular phosphoglycoproteins |
| 7 | P31150 | GDI1 | GDP dissociation inhibitor 1 |
| 8 | Q16653 | MOG | Myelin sheath oligodendrocyte glycoproteins |
| 9 | Q9BYH1 | SEZ6L | Seizure-related 6 homolog-like protein |
| 10 | Q16799 | RTN1 | reticuloendothelin 1 |
| 11 | Q8WXD2 | SCG3 | Secreted granin III |
| 12 | P09104 | ENO2 | Enolase 2 |
| 13 | Q14982 | OPCML | Opioid-binding protein/cell-adhesion molecule-like protein |
| 14 | Q92686 | NRGN | Neuroparticle protein |
| 15 | P23471 | PTPRZ1 | Protein tyrosine phosphatase receptor type Z1 |
| 16 | O14594 | NCAN | Neurocan. |

19. The method of claim 18, wherein the final quantified proteome data set further includes biomarkers listed in Table 4:

TABLE 4

| No. | Protein No. | Gene | Protein description |
|---|---|---|---|
| 1 | P02790 | HPX | Hemopexin |
| 2 | P02768 | ALB | Albumin |
| 3 | P02647 | APOA1 | Apolipoprotein A1 |
| 4 | P01024 | C3 | Complementary C3 |
| 5 | P01011 | SERPINA3 | Serine protease inhibitor family A member 3 |
| 6 | P02765 | AHSG | α2-HS glycoprotein |
| 7 | P02774 | GC | GC, a vitamin D-binding protein |
| 8 | P02652 | APOA2 | Apolipoprotein A2 |
| 9 | P04004 | VTN | Vitronectin |
| 10 | P01042 | KNG1 | Kininogen-1 |
| 11 | P04217 | A1BG | α-1-B glycoprotein |
| 12 | P00734 | F2 | coagulation factor II, thrombin |
| 13 | Q14624 | ITIH4 | α-trypsin inhibitor heavy chain family member 4 |
| 14 | P02749 | APOH | apolipoprotein H |
| 15 | P19823 | ITIH2 | α-trypsin inhibitor heavy chain 2 |
| 16 | P02760 | AMBP | α-1-microglobulin/uropancreatic pancreas, enzymoin precursor |
| 17 | P00450 | CP | ceruloplasmin |
| 18 | P02656 | APOC3 | Apolipoprotein C3 |
| 19 | P01008 | SERPINC1 | Serine protease inhibitor family C member 1 |
| 20 | P05155 | SERPING1 | Serine protease inhibitorf amily G member 1 |
| 21 | P00747 | PLG | Profibrinolysin |
| 22 | P02753 | RBP4 | Retinol-binding protein 4 |
| 23 | P08603 | CFH | Complement factor H |
| 24 | P00751 | CFB | Complement factor B |
| 25 | P02654 | APOC1 | Apolipoprotein C1 |
| 26 | P04003 | C4BPA | Complement component 4-binding protein α |
| 27 | P19827 | ITIH1 | α-trypsin inhibitor heavy chain 1 |
| 28 | P08697 | SERPINF2 | Serine protease inhibitor family F member 2 |
| 29 | P05546 | SERPIND1 | Serine protease inhibitor family D member 1 |
| 30 | P43652 | AFM | Afarin |
| 31 | P04196 | HRG | Histidine-rich glycoproteins |
| 32 | P01019 | AGT | Hypertensin precursor |
| 33 | P02748 | C9 | Complementary C9 |
| 34 | P02655 | APOC2 | Apolipoprotein C2 |

TABLE 4-continued

| Protein No. | No. | Gene | Protein description |
|---|---|---|---|
| 35 | P03952 | KLKB1 | Mallikrein B1 |
| 36 | P08185 | SERPINA6 | Serine protease inhibitor family A member 6 |
| 37 | P02750 | LRG1 | Leucine-rich α-2-glycoprotein 1 |
| 38 | P01031 | C5 | Complementary C5 |
| 39 | Q96PD5 | PGLYRP2 | Peptidoglycan recognition protein 2 |
| 40 | Q03591 | CFHR1 | Complement factor H-associated protein 1 |
| 41 | P13671 | C6 | Complementary C6 |
| 42 | O95445 | APOM | Apolipoprotein M |
| 43 | P22792 | CPN2 | Carboxypeptidase N subunit 2 |
| 44 | P01009 | SERPINA1 | Serine protease inhibitor family A member 1 |
| 45 | P35858 | IGFALS | Insulin-like growth factor binding protein unstable subunits |
| 46 | P35542 | SAA4 | Serum amyloid protein A4, constitutively |
| 47 | P02787 | TF | Transferrin |
| 48 | P20851 | C4BPB | Complement component 4-binding protein β |
| 49 | P27169 | PON1 | Paraoxonase 1 |
| 50 | Q06033 | ITIH3 | Trypsin inhibitor heavy chain 3 |
| 51 | P00748 | F12 | blood coagulation factor XII |
| 52 | Q14520 | HABP2 | Hyaluronan-binding protein 2 |
| 53 | P00742 | F10 | blood coagulation factor X |
| 54 | P07358 | C8B | Complement C8 β chain |
| 55 | P06681 | C2 | Complementary C2 |
| 56 | P07360 | C8G | Complement C8 γ chain |
| 57 | Q96IY4 | CPB2 | Carboxypeptidase B2 |
| 58 | P02743 | APCS | Serum amyloid P fraction |
| 59 | P05543 | SERPINA7 | Member of the serine protease inhibitor family A 7 |
| 60 | P07357 | C8A | Complement C8 α chain |
| 61 | P80108 | GPLD1 | Glycosylphosphatidylinositol-specific phospholipase D1 |
| 62 | P15169 | CPN1 | Carboxypeptidase N subunit 1 |
| 63 | Q02985 | CFHR3 | Complement factor H-associated protein 3 |
| 64 | P06276 | BCHE | Butyryl cholinesterase (BUCHE) |
| 65 | P02671 | FGA | α-chain fibrinogen |
| 66 | P26927 | MST1 | # Not applicable |
| 67 | P55056 | APOC4 | Apolipoprotein C4 |
| 68 | P01344 | IGF2 | Insulin-like growth factor 2 |
| 69 | P00740 | F9 | Blood coagulation factor IX |
| 70 | P00738 | HP | Haptoglobin |
| 71 | P08519 | LPA | Lipoprotein (a) |
| 72 | P05160 | F13B | Coagulation factor XIII B-chain |
| 73 | Q04756 | HGFAC | HGF activator |
| 74 | P03951 | F11 | Blood coagulation factor XI |
| 75 | P20742 | PZP | PZP, a α-2-macroglobulin-like form |
| 76 | P19652 | ORM2 | Oral mucin 2 |
| 77 | P36980 | CFHR2 | Complement factor H-associated protein 2 |
| 78 | P02679 | FGG | γ-chain fibrinogen |
| 79 | Q9UK55 | SERPINA10 | Serine protease inhibitor family A member 10 |
| 80 | P11226 | MBL2 | Mannose-binding lectin 2 |
| 81 | P02675 | FGB | β-chain fibrinogen |
| 82 | Q9UGM5 | FETUB | Fetuin B |
| 83 | P02763 | ORM1 | Oral mucin 1 |
| 84 | P22891 | PROZ | Protein Z, a vitamin K-dependent plasma glycoprotein |
| 85 | O00187 | MASP2 | Mannnitol binds lectin serine peptidase 2 |
| 86 | P04070 | PROC | Protein C, the inactivation agent of the coagulation factors Va and VIIIa |
| 87 | P18428 | LBP | Lipopolysaccharide binding protein |
| 88 | Q13790 | APOF | Apolipoprotein F |
| 89 | P02741 | CRP | C reactive protein |
| 90 | Q9BXR6 | CFHR5 | Complement factor H correlation 5 |
| 91 | Q92496 | CFHR4 | Complement factor H correlation 4 |
| 92 | Q13103 | SPP2 | Secretory phosphoprotein 2 |
| 93 | P08709 | F7 | blood coagulation factor VII |
| 94 | Q9Y6Z7 | COLEC10 | Member of the lectin subfamily 10 |
| 95 | Q15485 | FCN2 | Fikelin 2 |
| 96 | Q76LX8 | ADAMTS13 | ADAM with platelet reactive protein type 13 motif, metalopeptidase |
| 97 | P55103 | INHBC | Arrestin β C subunit |
| 98 | Q86U17 | SERPINA11 | Serine protease inhibitor family A member 11 |
| 99 | Q15166 | PON3 | Paraoxonase 3 |
| 100 | P03950 | ANG | Angiogenin |
| 101 | Q8WWZ8 | OIT3 | Oncoprotein-inducible transcript 3 |
| 102 | Q969E1 | LEAP2 | Liver enrichment enriched antimicrobial peptides 2 |
| 103 | P00739 | HPR | Binding globin-associated proteins |
| 104 | P07307 | ASGR2 | Dessialate glycoprotein receptor 2 |
| 105 | P0DJI9 | SAA2 | Serum amyloid protein A2 |
| 106 | Q08830 | FGL1 | Fibrinogen-like 1 |
| 107 | Q9Y5C1 | ANGPTL3 | Angiogenin-like 3 |
| 108 | O14960 | LECT2 | Leukocyte-derived chemokine 2 |
| 109 | Q8NI99 | ANGPTL6 | Angiogenin-like 6 |
| 110 | P34096 | RNASE4 | Ribonuclease A family member 4 |
| 111 | P23141 | CES1 | Carboxylate enzyme 1 |
| 112 | A6NLP5 | TTC36 | Tetrapeptide repeat domain 36 |
| 113 | Q6Q788 | APOA5 | Apolipoprotein A5 |
| 114 | P07306 | ASGR1 | Dessialate glycoprotein receptor 1 |
| 115 | P36222 | CHI3L1 | Chitinase 3-like 1 |
| 116 | P11150 | LIPC | Hepatic-type lipase C |
| 117 | P58166 | INHBE | Arrestin βE subunit |
| 118 | P32754 | HPD | 4-hydroxyphenylpyruvate dioxygenase |
| 119 | Q9UBQ7 | GRHPR | Glyoxylate and hydroxypyruvate reductase |
| 120 | P81172 | HAMP | Iron modulin antimicrobial peptide |
| 121 | O15467 | CCL16 | C-C motif chemokine ligand 16 |
| 122 | Q7Z4W1 | DCXR | Diyl and L-cellulose reductase |
| 123 | Q9UK05 | GDF2 | Growth and differentiation factor 2 |
| 124 | P08319 | ADH4 | Ethanol dehydrogenase 4 (class II), pi-polypeptide. |

* * * * *